(12) United States Patent
Sufyan et al.

(10) Patent No.: US 12,295,825 B2
(45) Date of Patent: May 13, 2025

(54) IMPLANTABLE MEDICAL SYSTEM

(71) Applicant: IPENGINE MANAGEMENT (INDIA) PRIVATE LIMITED, New Delhi (IN)

(72) Inventors: Mohammad Sufyan, New Delhi (IN); Rajeev Malhotra, Newton, MA (US); Lee Richstone, New York, NY (US); Manish Vira, New York, NY (US)

(*) Notice: Subject to any disclaimer, the term of this patent is extended or adjusted under 35 U.S.C. 154(b) by 0 days.

(21) Appl. No.: 18/205,516

(22) Filed: Jun. 3, 2023

(65) Prior Publication Data

US 2024/0138968 A1 May 2, 2024

Related U.S. Application Data

(63) Continuation of application No. 16/871,402, filed on May 11, 2020, now Pat. No. 11,701,211, which is a
(Continued)

(30) Foreign Application Priority Data

Jun. 26, 2014 (IN) .......................... 1715/DEL/2014

(51) Int. Cl.
*A61F 2/00* (2006.01)
*A61B 5/20* (2006.01)
(Continued)

(52) U.S. Cl.
CPC ............ *A61F 2/0045* (2013.01); *A61B 5/205* (2013.01); *A61F 2/0027* (2013.01);
(Continued)

(58) Field of Classification Search
CPC ... A61F 2002/0068; A61B 2017/00805; A61B 5/205; A61N 1/36007
See application file for complete search history.

(56) References Cited

U.S. PATENT DOCUMENTS

| 6,050,937 A | 4/2000 | Benderev |
| 2004/0242956 A1* | 12/2004 | Scorvo .................. A61F 2/0022 |
| | | 600/38 |

(Continued)

FOREIGN PATENT DOCUMENTS

EP 2092912 A1 * 8/2009 ........... A61F 2/0036

*Primary Examiner* — Thaddeus B Cox
(74) *Attorney, Agent, or Firm* — NextWave IP Legal Services, LLC; Leon Fortin, Jr.

(57) ABSTRACT

An implantable system for managing urinary incontinence includes a sling with an elongate body member having a proximal portion, a distal portion and an intermediate portion. The intermediate portion is configured to be positioned underneath urethra of a subject for providing an adequate support to prevent leakage of urine during a stress event. A pressure sensor communicatively coupled with the elongated body member is configured to be positioned in an abdominal cavity and adapted to sense an increase in intra-abdominal pressure. The pressure sensor generates a first signal that is indicative of a change in the intra-abdominal pressure upon occurrence of the stress event. A processing circuit processes the first signal sensed by the pressure sensor and generates a second signal causing an adjustment of tensioning force in the elongate body member thereby changing magnitude of a supporting force to the urethra.

9 Claims, 16 Drawing Sheets

Related U.S. Application Data continuation of application No. 15/322,160, filed as application No. PCT/IN2015/050053 on Jun. 25, 2015, now Pat. No. 10,682,214.

(51) Int. Cl.
*A61B 17/34* (2006.01)
*A61N 1/05* (2006.01)
*A61N 1/36* (2006.01)

(52) U.S. Cl.
CPC ..... *A61B 17/3468* (2013.01); *A61F 2230/006* (2013.01); *A61F 2240/002* (2013.01); *A61F 2250/0018* (2013.01); *A61F 2250/0023* (2013.01); *A61N 1/0514* (2013.01); *A61N 1/36007* (2013.01)

(56) References Cited

U.S. PATENT DOCUMENTS

| | | |
|---|---|---|
| 2008/0242918 A1 | 10/2008 | Gross et al. |
| 2009/0012351 A1* | 1/2009 | Anderson ......... A61M 39/0208 606/157 |
| 2009/0259092 A1 | 10/2009 | Ogdahl et al. |
| 2010/0179576 A1* | 7/2010 | Halevy ................ A61F 2/0063 606/151 |
| 2010/0292718 A1* | 11/2010 | Sholev ................. A61F 2/0063 606/151 |
| 2011/0004049 A1 | 1/2011 | et al. |
| 2012/0215058 A1 | 8/2012 | Alexander |
| 2013/0006049 A1* | 1/2013 | Alexander ........... A61F 2/0045 600/37 |
| 2016/0038268 A1 | 2/2016 | Yachia et al. |
| 2016/0113754 A1* | 4/2016 | Lamraoui ................ A61F 2/04 606/157 |

* cited by examiner

IMPLANTABLE MEDICAL SYSTEM

CROSS-REFERENCE TO RELATED APPLICATIONS

This application is a continuation of U.S. patent application Ser. No. 16/871,402 filed on May 11, 2020, which is a continuation of U.S. patent application Ser. No. 15/322,160 filed on Dec. 26, 2016 and patented on as U.S. Pat. No. 10,682,214, which is a National Stage Entry of PCT/IN2015/050053 filed on Jun. 25, 2015, which claims priority to IN patent application No 1715/DEL/2014 filed Jun. 26, 2014. The complete disclosure of each preceding application, in its entirety, is herein incorporated by reference:

BACKGROUND

Field

The present invention generally relates to medical devices and more particularly relates to implantable medical devices and surgical procedures for deploying the implantable medical devices in a patient's body for repair of urinary incontinence, and methods for functioning of the implantable medical devices.

Description of the Related Art

Urinary Incontinence is a medical area of increasing importance especially in women. Stress urinary incontinence is a condition in which a patient leaks urine when a sudden increase in abdominal pressure occurs. The increase in pressure can occur due to various routine activities.

Various treatment options have been provided for stress urinary incontinence. Current treatment options for stress urinary incontinence include surgical as well as non-surgical options. For example, sub-urethral slings may be used to treat stress urinary incontinence by creating a support to the urethra and bladder neck. A sling tries to increase urethral closure pressure during stress to mitigate an involuntary loss of urine. In this surgical procedure, a sling hanging from and secured to pubo-abdominal side is used to support the urethra from below.

Though the pubovaginal sling procedures have been effective in returning continence to women, but additional support by the slings permanently and all the time may cause severe damages such as infection, erosion, irritation etc. The body may reject the slings in some cases. Moreover, the support provided by the slings may not be in accordance with requirements at a particular instant.

In view of the above, there is a need for an improved medical implant and a medical system for providing adequate support to urethra or bladder neck for repair of urinary incontinence.

SUMMARY

The present invention provides an automatically controlled implantable system for managing urinary incontinence. The system includes a sling with an elongate body member having a proximal portion, a distal portion and an intermediate portion, wherein the intermediate portion is configured to be positioned underneath the urethra of a subject for providing an adequate support to prevent leakage of urine during a stress event. The system may further include a pressure sensor communicatively coupled with the elongated body member and configured to be positioned in an abdominal cavity and adapted to sense an increase in intra-abdominal pressure transferred from the abdominal cavity. The pressure sensor generates a first signal that is indicative of a change in the intra-abdominal pressure upon occurrence of the stress event. The system further includes a processing circuit to process the first signal sensed by the pressure sensor. The processing circuit is configured to generate a second signal causing an adjustment of tensioning force in the elongate body member thereby changing magnitude of a supporting force to the urethra. In an embodiment, the system may include an elastomeric tube that is fabricated monolithically with the elongate body member. The tube may include a lumen there-through for allowing circulation of a fluid, wherein the circulation of fluid allows adjustments in the tensioning force in response to the second signal received from the processing circuit. In an embodiment, the system may include a shape memory polymer member at least one of coupled with and integrated with the elongate body member. The shape memory polymer member may be configured to deform from an initial state to a second state in response to the second signal received from the processing circuit. The deformation in the shape memory polymer member allows for adjustments in the tensioning force provided to the elongate body member upon occurrence of the stress event.

The present invention provides a subject-controlled implantable system for managing urinary incontinence. The system may include a urinary sling with an elongate body member having a proximal portion, a distal portion and an intermediate portion. The intermediate portion of the elongate body member is configured to be positioned underneath the urethra of a subject for providing an adequate support to prevent leakage of urine during a stress event. The system may include a trigger unit subcutaneously placed and configured to be activated manually by a subject upon his desire arising out of changing abdominal pressures transferring from an abdominal cavity. The trigger unit may be configured to generate a first signal upon activation by the subject. The system may further include a processing circuit to process the first signal. The processing circuit is configured to generate a second signal to request an adjustment of tensioning force in the elongate body member thereby changing magnitude of a supporting force to the urethra. In an embodiment, the system may include an elastomeric tube that is fabricated monolithically with the elongate body member. The tube may include a lumen there-through for allowing circulation of a fluid, wherein the circulation of fluid allows adjustments in the tensioning force in response to the second signal received from the processing circuit. In an embodiment, the system may include a shape memory element at least one of coupled with and integrated with the elongate body member. The shape memory element may be configured to deform from an initial state to a second state in response to the second signal received from the processing circuit. The deformation in the shape memory element allows for adjustments in the tensioning force provided to the elongate body member upon occurrence of the stress event.

BRIEF DESCRIPTION OF THE FIGURES

The invention and the following detailed description of certain embodiments thereof may be understood with reference to the following figures.

DETAILED DESCRIPTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The terms "a" or "an," as used herein, are defined as one or more than one. The term "another," as used herein, is defined as at least a second or more. The terms "including" and/or "having", as used herein, are defined as comprising (i.e., open transition).

In some embodiments, the present invention may be implemented in slings suitable for the treatment of male and female urinary incontinence employing a variety of surgical approaches. For example, female pelvic floor repair slings such as urinary slings may be implanted by techniques that involve transvaginal, transobturator, suprapubic, pre-pubic, or transperineal exposures or pathways, and male urinary incontinence slings may be implanted by techniques that involve transobturator, suprapubic, or transperineal pathways. The disclosed embodiments can be used as fecal incontinence slings which may be implanted by techniques that involve transvaginal, transobturator, suprapubic or via perineal floor pathways or through other methods or may be used for other uplift and reconstruction surgeries. In some embodiments, the invention may be implemented in various other devices such as sphincters etc used for pelvic floor repair and incontinence repair.

Figure 1:
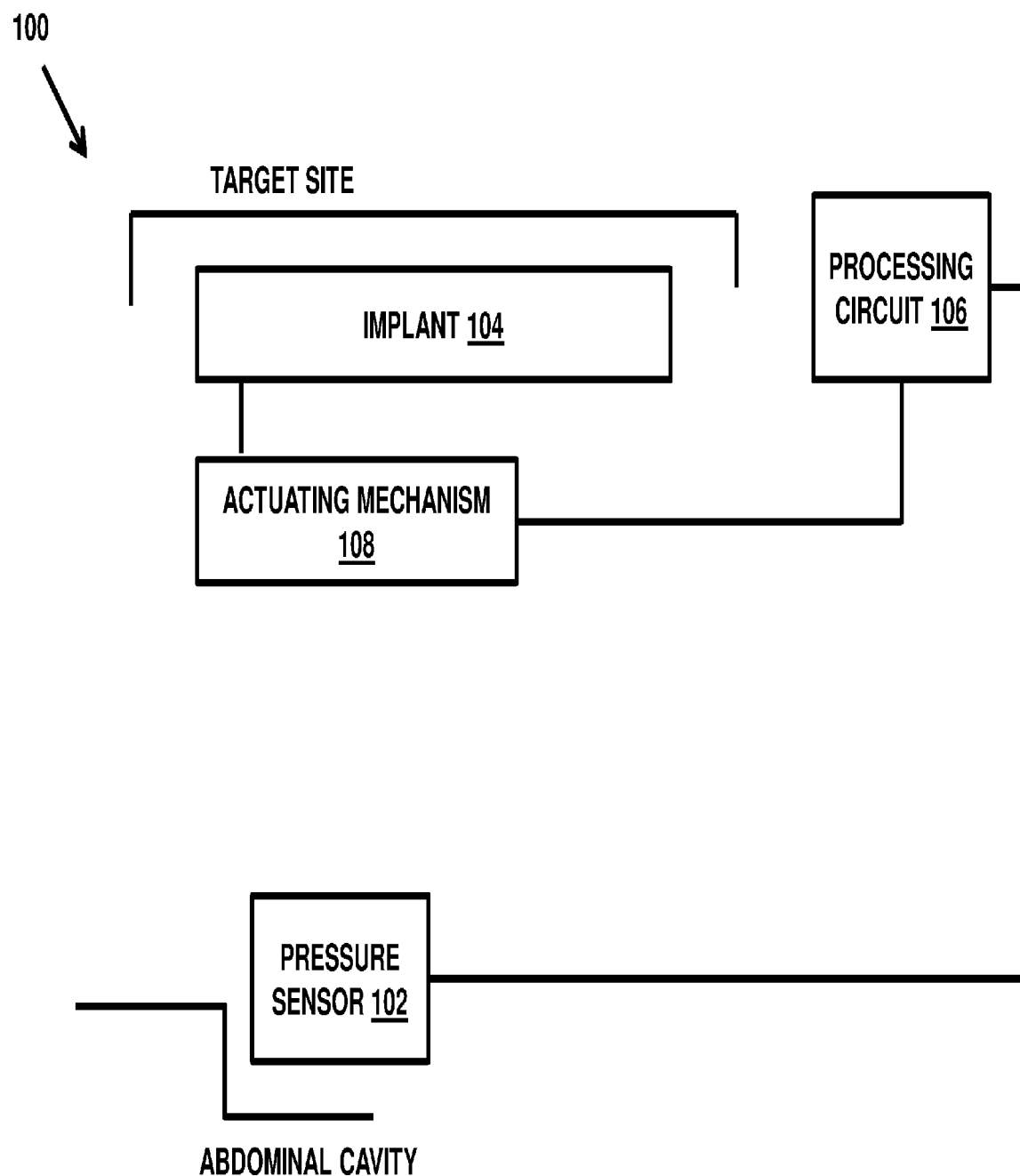
FIG. 1 illustrates a schematic diagram of an implantable system in accordance with an embodiment of the present invention.

FIG. 1 illustrates a schematic diagram of an implantable medical system (interchangeably referred to as implantable system or system) 100 in accordance with an embodiment of the present invention. The implantable system 100 may include a pressure sensor 102 positioned in an abdominal cavity, an implant 104 located proximate a target site, a processing circuit 106 communicatively connected with the pressure sensor 102, and an actuating mechanism 108 operatively or communicatively connected with the implant 104 and the processing circuit 106.

In accordance with various embodiments, the implant 104 may be a urinary sphincter, a sling such as a mesh-based sling for urinary incontinence, a non-mesh-based sling made of synthetic or natural material for urinary incontinence.

The pressure sensor 102 may be located in or around or proximate the abdominal cavity and configured to sense an intra-abdominal pressure or pressure changes. For example, the pressure sensor 102 may be configured to sense intra-abdominal pressure rises above a certain defined value that may cause incontinence. The intra-abdominal pressure may rise due to events or activities such as coughing, laughing, sneezing, or other activities hereafter referred to as pressure events or stress events. In an embodiment, the implantable system 100 may be activated only when a stress event or a pressure event occurs such that the pressure sensor 102 senses an increase in the intra-abdominal pressure otherwise the implantable system 100 may remain deactivated when the intra-abdominal pressure is within a defined range or does not pass the defined value that may cause urinary incontinence. A user may deactivate the implantable system 100 to allow voluntary bladder emptying that may require straining and increase in the intra-abdominal pressure by manually pushing a switch placed subcutaneously or by using a remote control. In an example, the pressure sensor 102 may be mounted to or proximate the bladder or to any other location if that gives a better reading of the intra-abdominal pressure or variations in the intra-abdominal pressure. The pressure sensor 102 may generate a first signal that is indicative of a change in the intra-abdominal pressure upon occurrence of the pressure event. The first signal may be sent to the processing circuit 106 to process the first signal sensed by the pressure sensor 102. The processing circuit 106 is configured to generate a second signal based on the first signal such that the second signal is sent to the actuating mechanism 108 to cause an adjustment of tensioning force in the implant 104 thereby changing magnitude of a supporting force to the target site, or to cause closing and/or opening at the target site or stimulation of the target site, based on the nature of implant 100 and functioning of the actuating mechanism 108.

In an example, the actuating mechanism 108 may include a stimulator to stimulate tissues at the target site electrically or electronically based on variations in the intra-abdominal pressure so as to allow contraction of the tissues such as proximate the urethra for avoiding leakage of urine during the stress event. In an example, the actuating mechanism 108 may include an elastomeric tube fabricated monolithically with the implant 104 or mounted separately on the implant 104. The elastomeric tube may include a lumen there-through for allowing circulation of a fluid such that the circulation of the fluid allows adjustments in the tensioning force in response to the second signal received from the processing circuit 106. In an example, the actuating mechanism 108 may include a ball valve configured to close or open passage of urine flow in response to the second signal received from the processing circuit 106 based on variations in the intra-abdominal pressure. In an example, the actuating mechanism 108 may include a shape memory polymer member or shape memory alloy member or any other shape memory element configured to deform between a first state and a second state in response to the second signal received from the processing circuit 106. The deformation in the shape memory polymer member or shape memory alloy member or shape memory element may allow for adjustments in the tensioning force provided to the implant 104 upon occurrence of the stress event. In an example, the actuating mechanism 108 may include a light-induced (also referred to as light responsive interchangeably) shape memory polymer member or a light-induced shape memory alloy member configured to deform between the first state and the second state in response to a light beam or photon received from a light source such that a deformation in the light-induced shape memory polymer member or light-induced shape memory alloy member allows for adjustments in the tensioning force provided to the implant 104 upon occurrence of the stress event.

The implantable system 100 may further include other auxiliary units or devices or components to facilitate interconnections among the various devices of the implantable system 100, to provide power supply, and to perform sensing or processing activities. For example, the implantable system 100 may include electrical and/or electronic circuitry for interconnections, switches for turning the system on or off placed subcutaneously and controlled by a user such as a subject, other control systems for allowing patient control functions, other sensors such as a sensor for monitoring bladder fullness, bladder emptiness etc, electrodes, resistors, power supply units, transducers, actuation devices contained in the actuation mechanism 108 (interchangeably referred to as actuating mechanism without limitations) for enabling functioning of the actuation mechanism 108 and several other devices or components for enabling functioning and performance of the implantable system 100 without limitations.

Several embodiments and variants of the implantable system 100 are illustrated and discussed in conjunction with various figures hereafter.

Figure 2A:
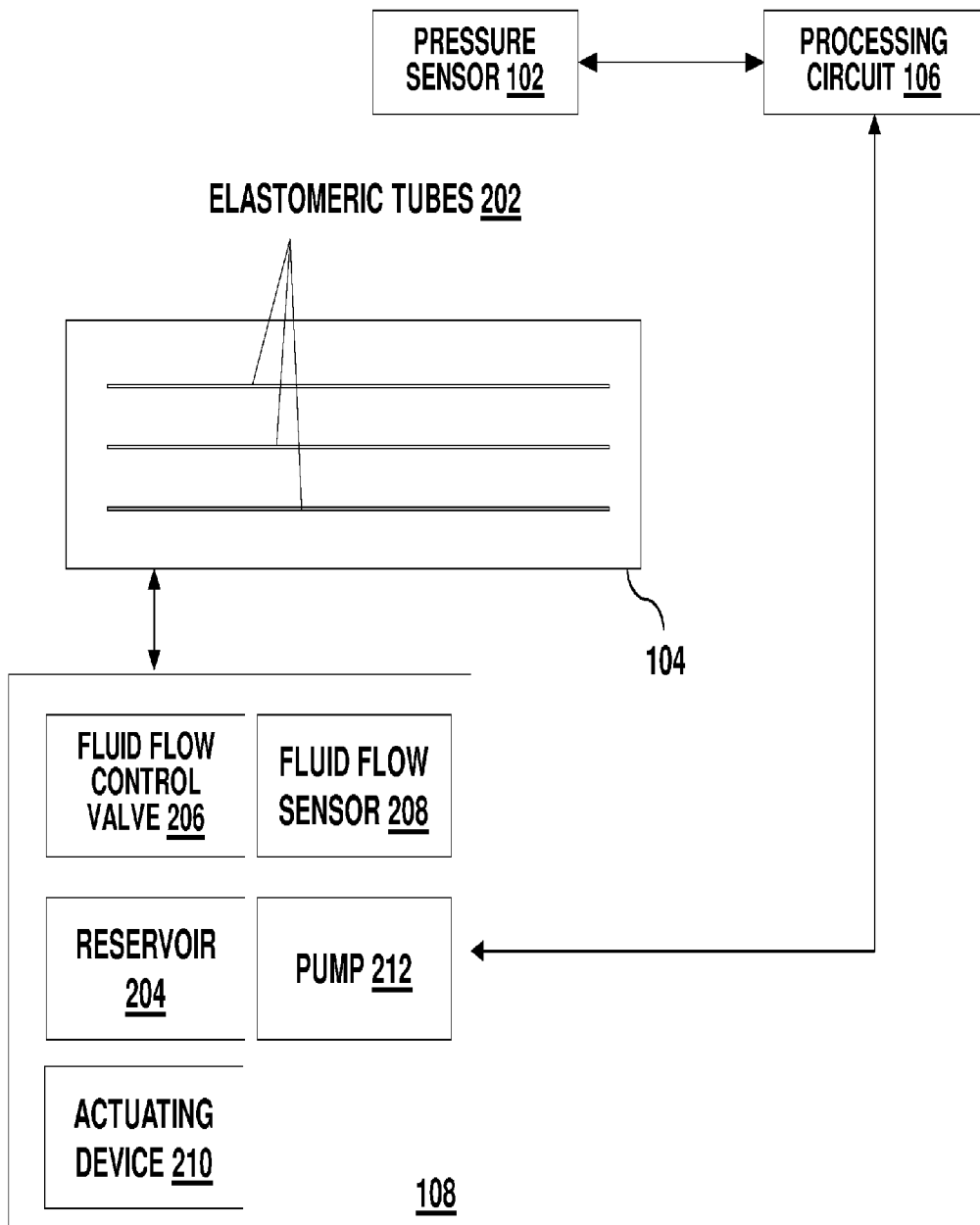
FIGS. 2A and 2B illustrate schematic diagrams of an implantable system in accordance with an embodiment of the present invention.
Figure 2B:
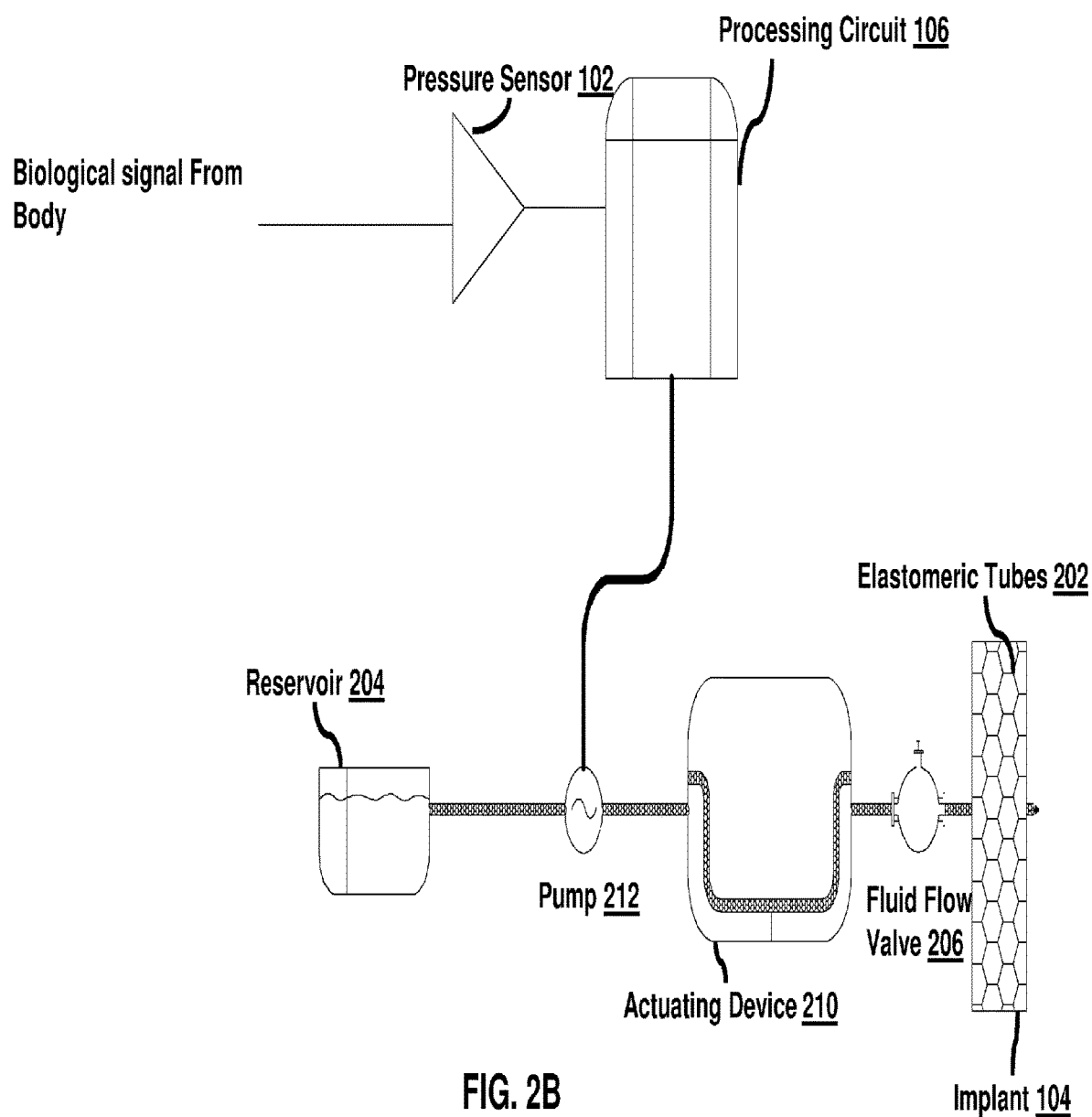

FIG. 2A and FIG. 2B illustrate schematic views of the implantable system 100, in accordance with an embodiment of the present invention, wherein the actuating mechanism 108 includes or is coupled to a plurality of elastomeric tubes 202 to control adjustment of the tensioning force in the implant 104 that supports the urethra or bladder neck or proximate tissues. In an example, the elastomeric tubes 202 may be coupled to the implant 104 removably. In an example, the elastomeric tubes 202 may be fabricated monolithically with the implant 104 such that the implant 104 and the elastomeric tubes 202 may be fabricated as a single component. Each of the elastomeric tubes 202 may include a lumen there-through for allowing circulation of a fluid that may be received from a reservoir 204 communicatively coupled to the elastomeric tubes 202. The elastomeric tubes 202 are configured to assume a first configuration (also referred to as a first state interchangeably) and a second configuration (also referred to as a second state interchangeably) based on whether the fluid is flowing through the lumen or not at a particular instant. In an example, the first configuration may represent an original state of the elastomeric tubes 202 when no fluid is flowing there-through and the second configuration may represent a deformed or expanded state when fluid enters in the lumen of the elastomeric tubes 202. In some embodiments, amount of fluid flowing there-though may define an extent of deformation in the elastomeric tubes 202 and accordingly the second configuration may assume different states depending on the amount of fluid flowing and the deformation in the elastomeric tubes 202. The first configuration and the second configuration may be altered by altering flow of the fluid through the lumen. For example, upon receipt of the fluid from the reservoir 204 and based on the amount of fluid flowing there-through, the elastomeric tubes 202 may expand to a defined extent thereby providing a defined support to the urethra or urethral tissues or bladder neck or other proximate tissues thus preventing flow of urine leakage. The elastomeric tubes 202 may regain their shape such as the first original configuration once the fluid is withdrawn back. The delivery and flow of the fluid from the reservoir 204 to the elastomeric tubes 202 and withdrawal of the fluid from the elastomeric tubes 202 back to the reservoir 204 may be controlled by the processing circuit 106 based on the first signal received from the pressure sensor 102 by the processing circuit 106 upon sensing of variations in the intra-abdominal pressure such that the processing circuit 106 generates and sends the second signal to the actuating mechanism 108 based on the first signal so as to regulate the flow of the liquid or any other fluid. The second signal may trigger the actuating mechanism 108 to regulate the flow of the fluid.

In an example, the actuating mechanism 108 may include a fluid flow control valve 206 operatively coupled to the reservoir 204, a fluid flow sensor 208 for monitoring the amount of fluid flowing through the fluid flow control valve 206 when the valve 206 is in open state, and an actuating device 210 optionally that may include other mechanical devices for actuating the flow of the fluid such as a piston cylinder arrangement, shafts, rods, crankshafts, or other devices. When the intra-abdominal pressure rises upon occurrence of the stress event, the processing circuit 106 may generate the second signal and cause the fluid flow control valve 206 to open thereby allowing the fluid to flow through the elastomeric tubes 202 to provide the supporting force or increase the tensioning force to provide additional or increased supporting force to the urethra or bladder neck or other proximate tissue. The second signal may be indicative of an amount of the supporting force required by the urethra or other tissues and accordingly a defined amount of the fluid may be allowed to pass through the elastomeric tubes 202 as controlled by the fluid flow sensor 208 after which the fluid flow control valve 206 may close automatically. After the intra-abdominal pressure decreases when the stress event is over, the processing circuit 106 may cause the fluid to be withdrawn from the elastomeric tubes 202 back into the reservoir 204. The reservoir 204 may be coupled operatively to an implantable pump 212 placed subcutaneously or at other location as appropriate to control the delivery and withdrawal of the fluid to/from the elastomeric tubes 202 based on the second signal. In accordance with various embodiments, various other mechanisms may be provided for the delivery and withdrawal of the fluid to/from the reservoir 204.

In an example, the reservoir 204 may include a port that may be coupled to a needle from externally for injecting the fluid into the reservoir 204 or withdrawing the fluid from the reservoir 204 to replace the fluid. The port may be coupled to the reservoir 204. The reservoir 204 may be contained in a housing along with the actuating device 210 and the pump 212. For example, the housing may enclose the reservoir 204, a cylinder, a piston coupled to the cylinder, rods and/or cam and/or gear arrangements for allowing circulation of the fluid through the pump 212. The volume of the fluid delivered from the reservoir 204 or withdrawn back into the reservoir 204 dictates position and movement of the piston within the cylinder and of the connecting rods. In an embodiment different components of the actuation mechanism 108 may be located in separate housings.

The reservoir 204 and other components of the actuation mechanism 108 may be implanted below the skin. A set of connecting tubes that may connect the actuation mechanism 108 with the elastomeric tubes 202 and various other communication leads or wires or circuitry for connecting various components and sub-components of the implantable system 100 may extend through tissues just under the skin or deep within the tissues based on requirements.

In an embodiment, the elastomeric tubes 202 may be positioned on a bottom surface of the implant 104. In an embodiment, the elastomeric tubes 202 may be positioned on a top surface of the implant 104. In an embodiment, when the fluid is passed through the elastomeric tubes 202, the elastomeric tubes 202 may extend in diameter thereby pushing the implant 104 toward the urethra or bladder neck so that the implant 104 exerts additional supporting force to the urethra or bladder neck. Once the fluid is withdrawn back, the diameter of the elastomeric tubes 202 may decrease leading to relaxing of the urethra or bladder neck.

Figure 3A:
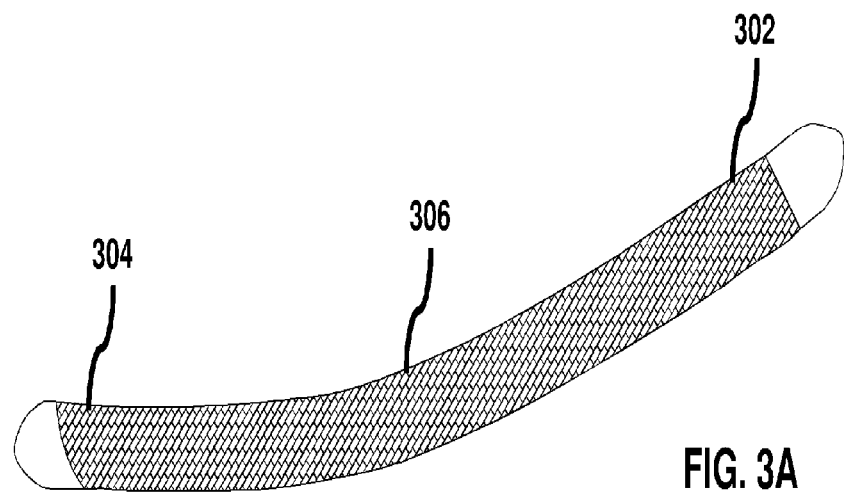
FIGS. 3A and 3B illustrate schematic diagrams of implants in accordance with some embodiments of the present invention.

FIG. 3A illustrates an embodiment of the implant 104. The implant 104 has a first portion 302, a second portion 304, and a mid portion 306 between the first portion 302 and the second portion 304 with a length of the implant 104 extending between the first portion 302 and the second portion 304 longitudinally. In an embodiment, as illustrated, the implant 104 is defined as a linear strip of mesh configured to provide support to the urethra or bladder neck or other tissues. In accordance with various embodiments, the implant 104 can have a variety of shapes such as rectangular, square, trapezoidal, and the like.

In some embodiments, the mid portion 306 of the implant 100 is de-tanged (without tangs). The length of the de-tanged section can vary based on surgical requirements or location of placement inside the patient's body. In some embodiments, the first portion 302 and the second portion 304 may include tangs such that upon placement of the implant 104, the first portion 302 and the second portion 304 of the implant 104 can interact with bodily tissues to help anchor or retain the implant 104 in position within the body of the patient. In some embodiments, the de-tanged section can be made by fusing threads or strands of a mesh edge together by heat. The de-tanged section may, in some embodiments, prevent unraveling of the implant 104 when in tension and thus limits its stretch.

In some embodiments, the implant 104 is made of a synthetic material such as a polymeric material and the like. In some embodiments, the implant 104 includes a polymeric mesh body. The mesh body may comprise a chain link fence-like design. In such designs, the fibers or strands of the mesh may be woven, linked, or otherwise connected, and may share the stress of a supported load. In some embodiments, the implant 104 may include a polymeric planar body without mesh cells and structures. Exemplary polymeric materials are polypropylene, polyester, polyethylene, nylon, PVC, polystyrene, and the like. In some embodiments, the implant 104 is made of a non-woven polymeric material. In some embodiments, the implant 104 can be made of natural materials such as biologic material or a cadaveric tissue and the like. Additionally, in some embodiments, the implant 104 is stretchable and flexible to adapt movements along the anatomy of the human body. In some embodiments, the implant can be made of biodegradable materials. In some embodiments, the implant can be made of non-biodegradable material. In some embodiments, the implant can be made of medical grade materials.

Figure 3B:
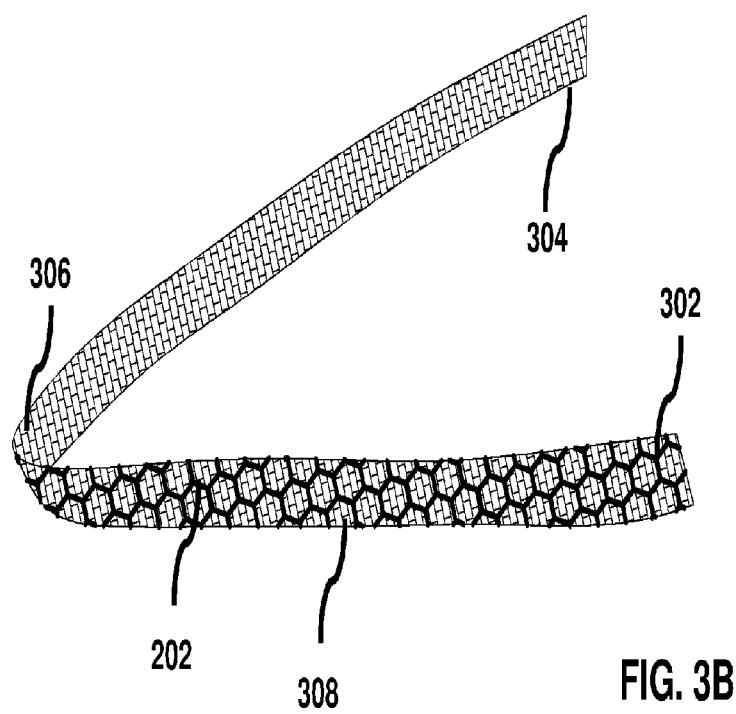

The implant 104 shown in FIG. 3A can be coupled with elastomeric tubes 202 separately. In an embodiment, the elastomeric tubes 202 may be integrated within a structure of the implant 104 itself. FIG. 3B illustrates an embodiment of the implant 104 in accordance with such an embodiment wherein the elastomeric tubes 202 may be integrated in the implant 104. As shown, the elastomeric tubes 202 are embedded within the implant 104 in the form of hexagonal cells. The hexagonal cells-shaped elastomeric tubes 202 may for example be structured as inflatable mesh portions such that upon receipt of the fluid, the inflatable mesh portions undergoes inflation and causes an increase in the tensioning force to provide adequate support and tension to the urethra or bladder neck or other tissues. In an embodiment, the elastomeric tubes 202 may be defined in another shape or may simply be constructed as linear members.

In an embodiment, the elastomeric tubes 202 may be positioned on a bottom surface 308 of the implant 104. When the fluid is passed through the elastomeric tubes 202, the elastomeric tubes 202 may extend in diameter thereby pushing the implant 104 toward the urethra or bladder neck so that the implant 104 exerts additional supporting force to the urethra or bladder neck. Once the fluid is withdrawn back, the diameter of the elastomeric tubes 202 may decrease leading to relaxing of the urethra or bladder neck.

Figure 4:
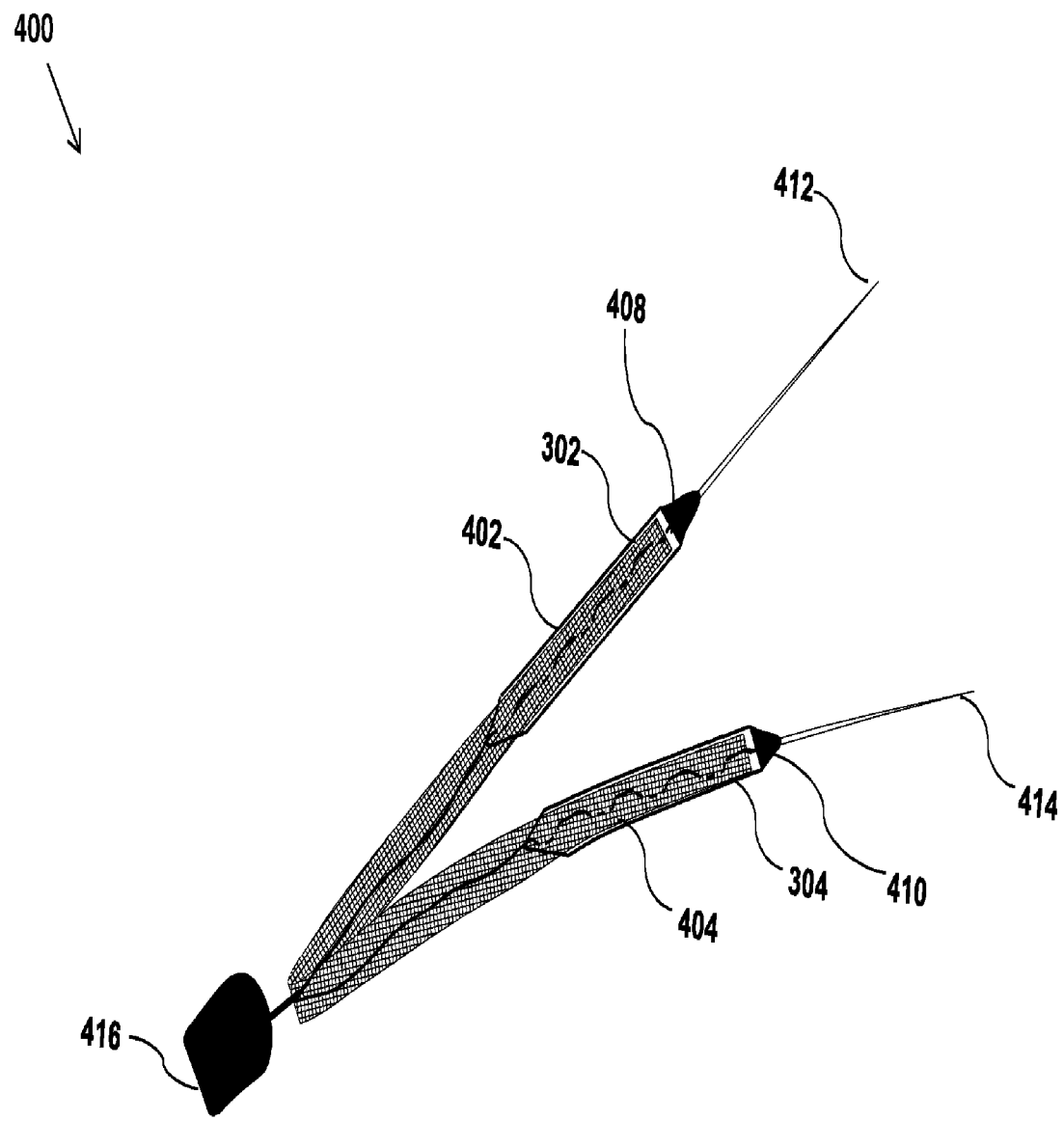
FIG. 4 illustrates a perspective view of a medical assembly including an implant in accordance with an embodiment of the present invention.

FIG. 4 illustrates a medical assembly 400 in an embodiment. The medical assembly 400 includes the implant 104, a first sleeve 402, a second sleeve 404, a tab 406, a first elongate member 408, and a second elongate member 410. The first sleeve 402 and the second sleeve 404 are configured to shield the first portion 302 and the second portion 304 of the implant 104. In some embodiments, the first sleeve 402 and the second sleeve 404 can be thin wall flat tubes. In some embodiments, the first sleeve 402 and the second sleeve 404 are made of polymer and may be colored for easy visualization. In some embodiments, the first sleeve 402 and the second sleeve 404 can be manufactured from an opaque or a transparent plastic film. The transparent plastic film enables visual examination of the implant 104. In an example, length of the first sleeve 402 is sufficient to envelop or shield the first portion 302 of the implant 104 and length of the second sleeve 404 is sufficient to shield the second portion 304 of the implant 104. In various embodiments, the first portion 302 is a first end portion of the implant 104 and the second portion 304 is the second end portion of the implant 104 such that the first sleeve 402 and the second sleeve 404 are configured to enclose the first end portion and the second end portion respectively of the implant 104. In certain embodiments of the present invention, the first and the second sleeves 402 and 404 shield only the first portion 302 and the second portion 304 of the implant 104 such that the mid portion 306 of the implant 104 remains un-shielded. The un-shielded mid portion 306 is configured to interact to a bodily tissue upon placement. The length of the implant 104 that is shielded with the sleeves 402 and 404 can vary based on requirements.

The medical assembly 400 may also include a first dilator 412 configured to be coupled to the first sleeve 402, and a second dilator 414 configured to be coupled to the second sleeve 404. The first dilator 412 and the second dilator 414 are configured to be coupled respectively to distal ends of the first sleeve 402 and the second sleeve 404. In some embodiments, the first dilator 412 and the second dilator 414 are further configured to be coupled to a delivery device (not shown). The delivery device can be used to facilitate delivery of the medical assembly 400 including the implant 104 within the patient's body. In some embodiments, the dilators 412 and 414 are small in diameter.

The medical assembly 400 further includes a tab 416 configured to be coupled to the implant 104. The tab 416 is configured to identify the mid portion 306 of the implant 104 and provide for equal length of the implant 104 on either side of a body tissue.

In certain embodiments, the first elongate member 408 is configured to removably couple the implant 104 with the first sleeve 402 and the second elongate member 410 is configured to removably couple the implant 104 with the second sleeve 404. The first elongate member 408 and the second elongate member 410 include one of a thread, a medical suture, a filament, a rope, and the like. The first sleeve 402 and the second sleeve 404 may be configured to be removably coupled to the implant 104 with a single elongate member in other embodiments. The sleeves 402 and 404 may be removed from the implant 104 by pulling the elongate members 408 and 410 thereby removing the sleeves 402 and 404 from the body after positioning and placement of the implant 104 in the body at the target site. The sleeves 402 and 404 may prevent the implant 104 from contaminations and thus may prevent the body from infection.

In embodiments, the implant 104 may include or be coupled to anchors, or tangs or other structures for facilitating positioning and fixation of the implant with bodily tissues. In some embodiments, the implant 104 may be fixed to tissues using glue, staples, stitches and the like.

Figure 5A:
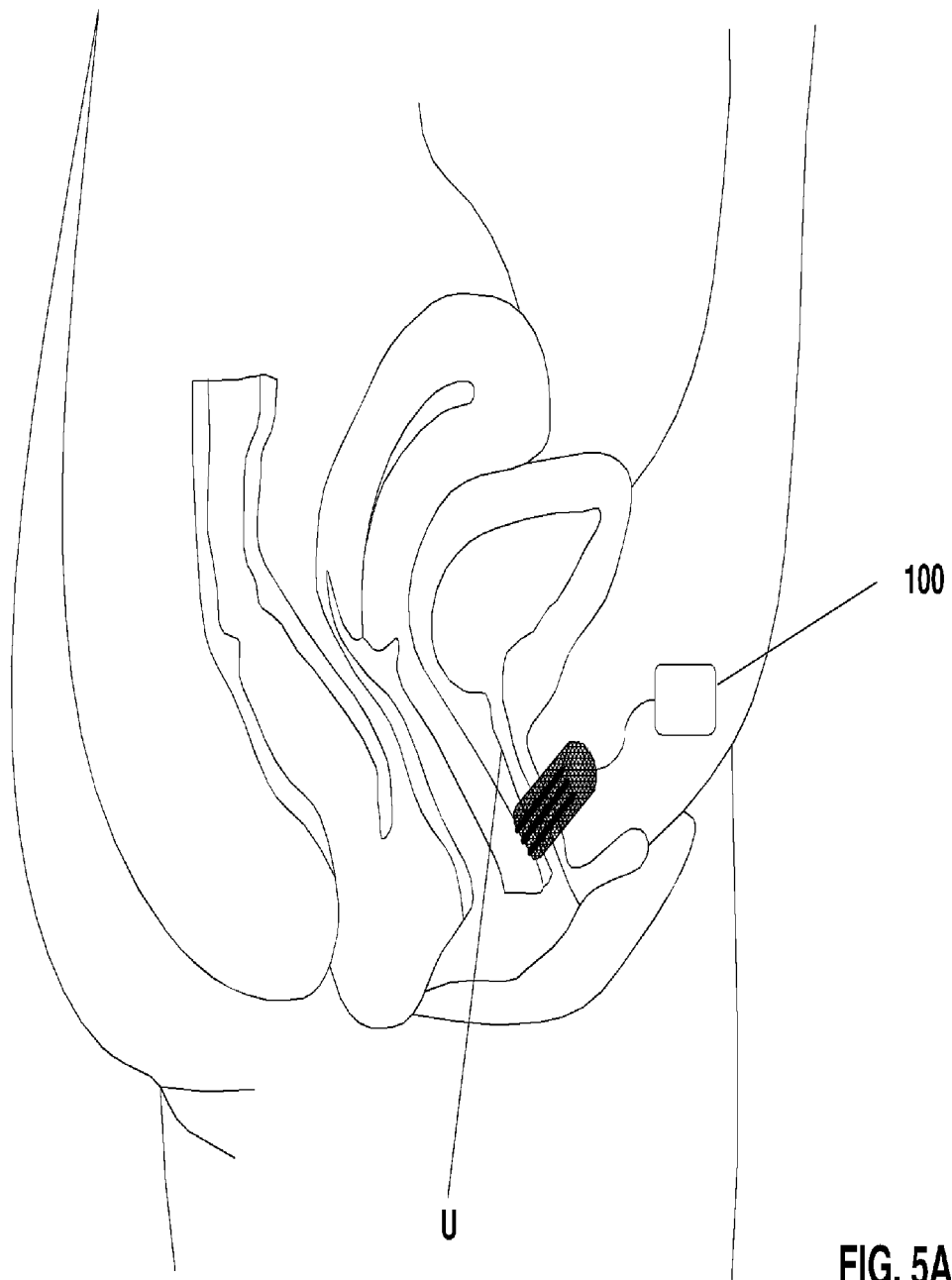
FIGS. 5A and 5B illustrate an implantable medical system positioned within a patient's body.
Figure 5B:
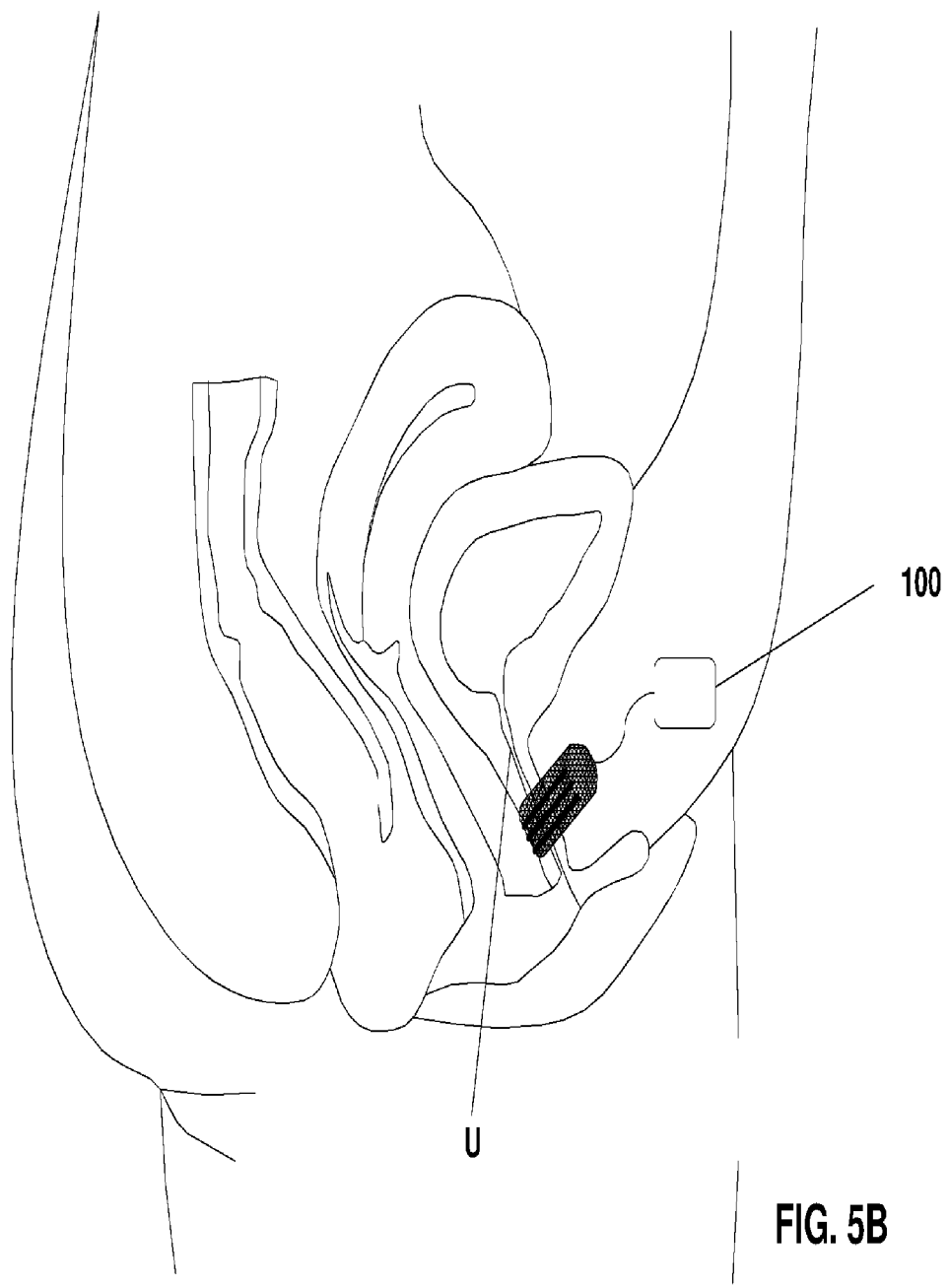

FIGS. 5A and 5B illustrate placement of the implantable system 100 of FIGS. 2A and 2B within a body of a female subject such that the implant 104 provides a support underneath the urethra U for controlling leakage of urine. FIG. 5A shows the urethra U in a relaxed state when the elastomeric tubes 202 are not fluid filled. FIG. 5B shows the urethra in a supported state to stop leakage of urine during a stress event by allowing the fluid to fill the elastomeric tubes 202. In accordance with the embodiments illustrated in FIGS. 2A-2B, and 5A-5B, various interconnections shown between various components or sub-systems may include electrical or electronic circuitry or wireless communication interfaces. For example, the processing circuit 106, pressure sensor 102, actuating mechanism 108, and the implant 104 may communicate through wireless mode, wired mode or a combination of both.

In an embodiment, the elastomeric tubes 202 may be connected with the reservoir 202 through hollow tubes that may allow circulation of the fluid. In an embodiment, the processing circuit 106 and the actuating mechanism 108 may be connected through electrical or electronic leads configured to transmit signals. In an embodiment, the processing circuit 106 and the actuating mechanism 108 may communicate through a wireless medium. In an example, the pressure sensor 102 may communicate with the processing circuit 106 through electric or electronic circuitry. In an example, the pressure sensor 102 and the processing circuit 106 may communicate wirelessly.

In an example, various components of the implantable system 100 may use wires or wireless radiofrequency telemetry to communicate with circuitry outside the body. In an example, intra-body communication among the various components may use conductive properties of the body to enable wireless communication. In an example, the various or at least some components may include or be connected with transmitters and/or receivers to receive and/or transmit signals from/to the various components of the implantable system 100 or from/to outside the body such as a remote controller. The implanted transmitters and receivers may be connected to equipment outside the body using a short wire or with wireless RF telemetry. In this way, less power may be needed to transmit and/or receive signals.

In an embodiment the implantable system 100 may be alternatively self-controlled or controlled by one or more local external control stations, at or near the location of the patient, and/or one or more remote external control stations, remote from the patient. Either or both of the local and remote stations may be operated by a person, such as a patient, a patient facilitator and/or a medical professional, or the stations may operate automatically. The remote station may include components such as a database for storing information useful for managing the implantable system 100, a processor, a memory, a transmitting/receiving device and/or wired connection for communicating with the one or more components of the implantable system 100, and a wireless link or combinations of these.

In an example, a system for the remote communication with the implantable system 100 may be used. The system may have a client PC that may receive data transmitted via internet from a server PC which may communicate with the implantable system 100 implanted into the body. The system particularly may permit the remote communication such that one or more device experts such as physicians and more experienced device users may be aware of the communication and provide guidance for subsequent interpretation and programming of the device.

In an example, a system that may enable high-frequency communication between an external communication device and the implantable system 100 or its various components may be used. The implantable system 100 implanted in a human patient may be in electrical communication with the patient by way of multiple leads or wires. Further the implantable system 100 may communicate with a standalone or offline programmer via short-range telemetry technology. The offline programmer may be equipped with a wand that, when positioned proximal to the implantable system 100, may communicate with the implantable system 100 through a magnetic coupling or by any other way.

In an embodiment, the various components of the implantable system 100 such as the pressure sensor 102 and the processing circuit 106 may communicate over a small bus having a minimum number of electrically conductive wires. For example, communication information, along with power and ground, may be provided over two conductive wires. At the same time, the implantable system 100 may operate by way of an internal power source, usually in the form of a battery, which may have a limited amount of available power. Moreover, because replacement of the implantable system 100 requires surgery to the patient, conservation of power is an important consideration. Further a communication unit may communicate with the components and send power as well as a synchronizing signal or clock signal to the components. The communication unit may also contain a transceiver to transmit and receive data over a communication bus. The communication unit may have protection networks to protect the implantable system 100 against transient voltages and currents.

Figure 6:
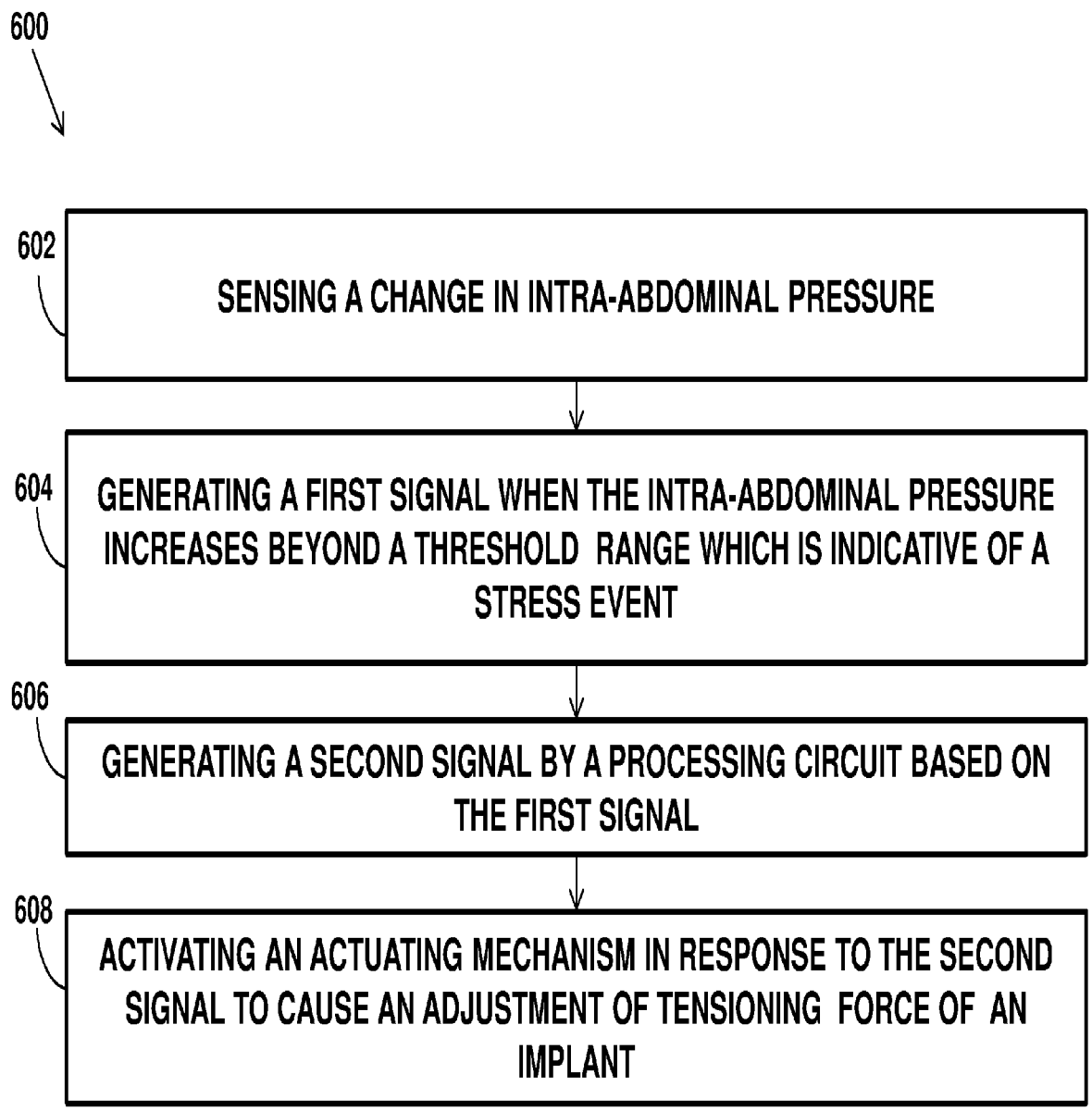
FIG. 6 illustrates a method diagram for operation of an implantable system in accordance with an embodiment of the present invention.

FIG. 6 illustrates a method diagram for operation of the implantable system 100 in accordance with an embodiment of the present invention. The method 600 of operation of the implantable system 100 is now described hereafter referring to above discussed FIGS. 1-5B. At step 602, the method 600 includes sensing a change in the intra-abdominal pressure. In an embodiment, the change in the intra-abdominal pressure may be sensed by the pressure sensor 102 located in or around or proximate to abdominal cavity. In some other embodiments, the pressure sensor 102 may be placed in or around or proximate to any other body cavity or to any other location if that gives a better reading of the intra-abdominal pressure or variations in the intra-abdominal pressure. The intra-abdominal pressure may rise due to events or activities, referred to as the pressure events or the stress events as discussed above.

At step 604, the method 600 includes generating the first signal when the intra-abdominal pressure increases beyond a threshold range which is indicative of the pressure or stress event. The first signal generated by the pressure sensor 102 may be indicative of the change in the intra-abdominal pressure upon occurrence of the pressure or stress event. The pressure sensor 102 may send the first sensed signal to the processing circuit 106 for further processing.

At step 606, the method 600 further includes generating the second signal by the processing circuit 106 based on the first signal. The method 600 may further include, at step 608, activating the actuating mechanism 108 in response to the second signal so that the actuation mechanism 108 of the implantable system 100 causes an adjustment of the tensioning force of the implant 104. The tensioning force may be adjusted such that the magnitude of the supporting force to the urethra or bladder neck or other tissues is adequate to control leakage of urine during the stress event. In accordance with an example, the second signal may activate the actuation mechanism 108 of FIGS. 2A-2B so that the actuation mechanism 108 may allow controlled circulation of the fluid through the elastomeric tubes 202 for adjustment of the supporting force. In accordance with various other embodiments, the actuation mechanism 108 may be different. A few other actuation mechanisms and stimuli to stimulate the actuation mechanisms in accordance with embodiments are discussed elsewhere in the document without limitations.

In accordance with various embodiments discussed herein, the implantable system or the implantable medical system 100 or other implantable medical systems as discussed later in different embodiments may provide several benefits. For example, the implantable medical system 100 may allow the implant 104 to provide only limited support as required at a particular instant of time based on intra-abdominal pressure variations. Intra-abdominal pressure may not always remain same and at times the intra-abdominal pressure may not be sufficient enough to cause leakage. In such situations, additional support to the urethra or bladder neck by the implant 104 may not be needed and may be undesirable. In some cases, the support may be needed only when a stress event occurs. In some cases, only a limited support may be needed when a stress event does not occur which may be lesser than provided otherwise. However, providing the support by deploying the implant 104 permanently without any variations in the tensioning force in view of the intra-abdominal pressure variations at different times may be harmful and undesirable and may even cause damage to tissues such as infection, erosion, contraction, extrusion, bleeding, irritation etc. Further, implants that are usually deployed conventionally may be tensioned for extreme conditions of stress and intra-abdominal pressures. However, such extreme conditions may occur only for a fraction of the total time implant remains inside the body.

The implantable system 100 as provided by the present invention allows to adjust tensioning of the implant 104 and provide adequate support only when needed and to an extend that is desirable. The implant 104 may thus not be required to support the urethra or bladder neck all the time or with same force at all times thereby allowing bodily tissues to relax and avoid interactions with the implant 104 when not needed.

Figure 7:
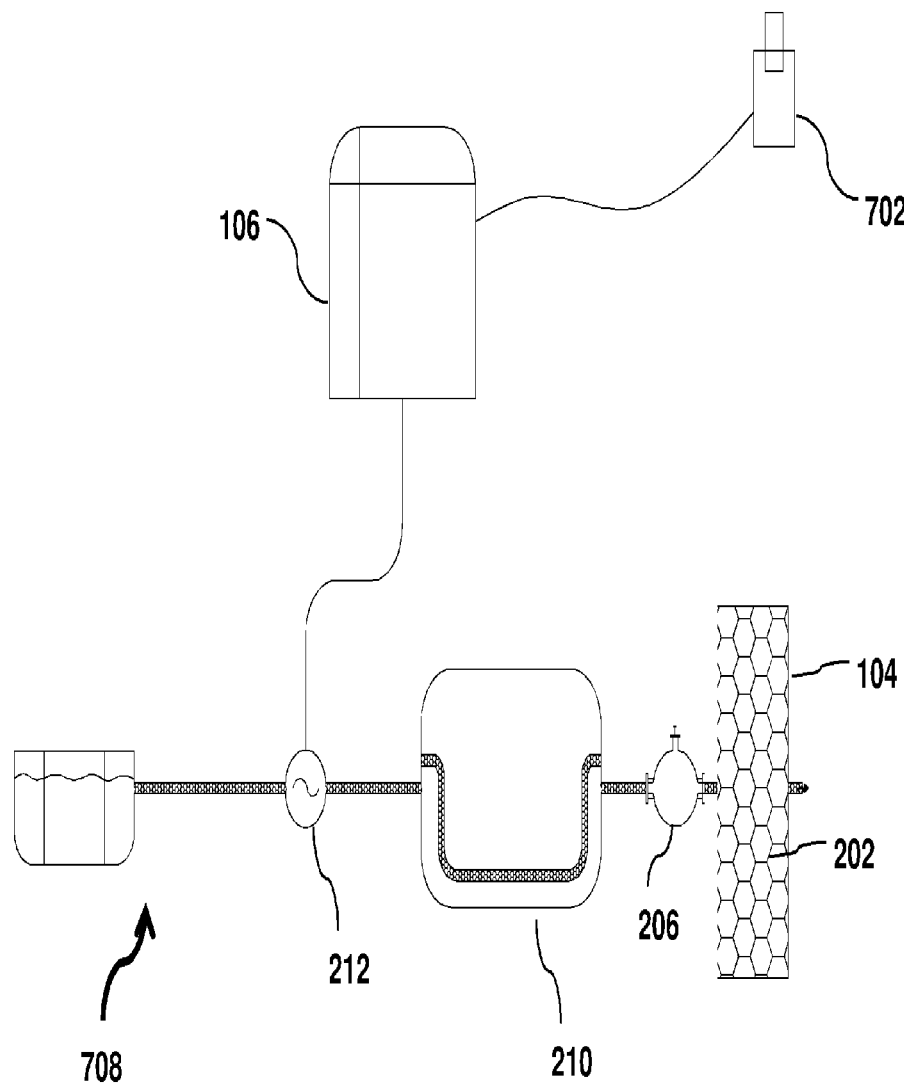
FIG. 7 illustrates a schematic diagram of an implantable system in accordance with an embodiment of the present invention.

FIG. 7 illustrates an implantable system 700 in accordance with an embodiment of the present invention. The implantable system 700 is configured to be activated based on a subject's input whenever the subject senses possibility of leakage of urine or an increase in the intra-abdominal pressure due to the stress event. As shown, the implantable system 700 includes the implant 104, a triggering unit 702, the processing circuit 106, and the actuating mechanism 108. The implant 202 may be similar to as shown in FIGS. 3A, 3B, 4, 5A, and 5B that may be configured to support urethra, bladder neck, or proximate tissues for preventing leakage of urine due to incontinence.

The triggering unit 702 may be positioned subcutaneously and may be accessible and configured to be activated by the subject from externally to control operation of the implantable system 700 by the subject voluntarily. The triggering unit 702 is configured to be accessed by the subject upon a desire arising out of changing abdominal pressures transferring from the abdominal cavity. The triggering unit 702 is configured to generate the first signal when activated by the subject manually. The first signal may be sent to the processing circuit 106 in a manner similar to as discussed above in conjunction with various embodiments. The processing circuit 106 may generate the second signal in response to the first signal. The second signal may include a request to be transmitted to the actuating mechanism 108 for causing an adjustment of the tensioning force in an elongate body member of the implant 104 thereby changing magnitude of the supporting force to the urethra or bladder neck to a defined value on the basis of requirements by the subject.

The actuating mechanism 108 may include the plurality of elastomeric tubes 202, the reservoir 204, the pump 212, the control valve 206, the actuating device 210, and other auxiliary components. In accordance with the embodiment illustrated in FIG. 7, the implantable system 700 may not include a switch similar to the switch discussed in conjunction with FIGS. 2A-2B as the subject may control operation of the implantable system 700 by activating the triggering unit 702 manually when desirable such as during passage of urine voluntarily the subject may avoid activation of the implantable system 700 and keep the elastomeric tubes 202 in original state with no fluid filled therein. In an embodiment, the positioning and placement of the actuating mechanism 108 may be different slightly from positioning of the actuating mechanism 108 of FIGS. 2A-2B if required so as to facilitate operation of the embodiment discussed herein without deviating from the spirit and scope of the present invention.

Figure 8:
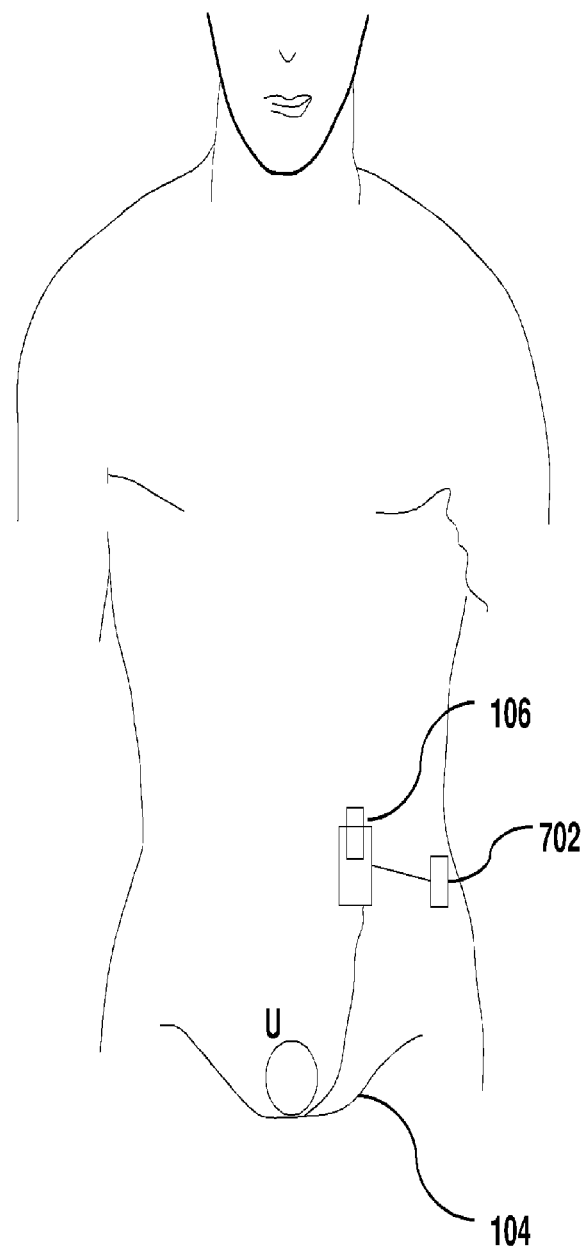
FIG. 8 illustrates an implantable system positioned within a patient's body in accordance with an embodiment of the present invention.

In an example, the actuating mechanism 108 and the triggering unit 702 may be communicatively coupled to the pressure sensor 102 (not shown in FIG. 7). Upon activation of the triggering unit 702 by the subject, the pressure sensor 102 may be adapted to sense the intra-abdominal pressure or variations in the intra-abdominal pressure transferred from the abdominal cavity such that a measure of the sensed intra-abdominal pressure or pressure variations may be used to determine a desired contraction or support in urethra or bladder neck or proximate tissues that may result in a necessary supporting force to the urethra or bladder neck. In accordance with this embodiment, while the activation of the actuating mechanism 108 may be manually triggered by the subject with the use of the triggering unit 702, the pressure sensor 102 may however allow the actuating mechanism 108 to vary degree of the tensioning force based on the sensed pressure, in an example. In other examples, the use of the pressure sensor 102 may be completely avoided and the actuating mechanism 108 may solely function based on activation of the triggering unit 702 so as to cause the implant 104 to assume one of the two states of the initial first state and the deformed second state. The deformed second state is achieved upon activation of the actuating mechanism 108 allowing circulation of the fluid through the elastomeric tubes 202. The actuating mechanism 108 may be communicatively coupled with the processing circuit 106 and may function in a manner similar to as discussed in conjunction with various figures above to process the first signal received from the triggering unit 702. In an example, the triggering unit 702 and the processing circuit 106 may be integrated as a single device. FIG. 8 illustrates a schematic view of positioning of the implantable system 700 of FIG. 7 in accordance with an embodiment of the present invention. The trigger unit 702 may be subcutaneously placed so as to be activated by applying a pressure such as by pressing with a hand of a user or subject from externally. The activation may contract or provide additional support to the urethra or bladder neck or proximate tissues in a similar manner as shown in FIG. 5B and prevent leakage of urine. Once the trigger unit 702 is deactivated such as by merely removing the applied pressure or by applying pressure once again that is by pressing the triggering unit 702 by hand once again, the support force to the implant 104 may be removed or reduced. In an example, the trigger unit 702 and the processing circuit 106 may be integrated in a single housing and positioned at the same location. In an example, as shown in FIG. 8, the processing circuit 106 and the trigger unit 702 may be located separately.

Figure 9:
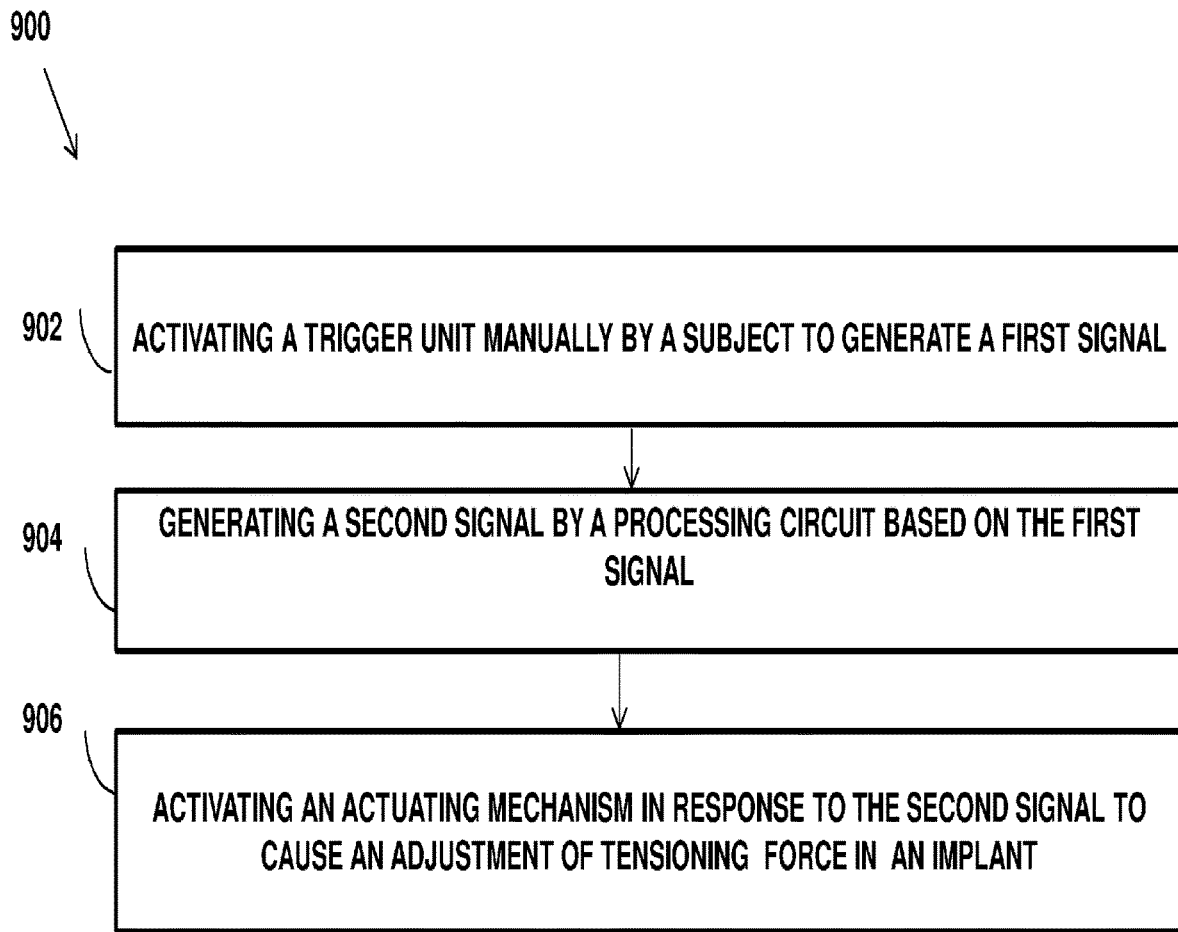
FIG. 9 illustrates a method diagram for operation of an implantable system in accordance with an embodiment of the present invention.

FIG. 9 illustrates a method flow diagram for managing the support to the urethra or bladder neck or other tissues by the implant 104 based on user desire such as during stress events when there is an increase in the intra-abdominal pressure which may cause leakage of urine if adequate support is not provided. The method 900 may include, at step 902, activating the trigger unit 702 manually by a subject to generate the first signal. For example, the subject may apply pressure on tissues from externally so that the trigger unit 702 placed subcutaneously may be activated upon application of the pressure or upon sensing of a biological touch resulting in generating the first signal. The first signal may be transmitted to the processing circuit 106. The processing circuit 106 may process the first signal and generate the second signal in a manner as explained earlier in conjunction with various figures at step 904. The method 900 may further include, at step 906, activating the actuation mechanism 108 in response to the second signal so that the actuation mechanism 108 of the implantable system 700 causes an adjustment of the tensioning force of the implant 104. The tensioning force may be adjusted such that the magnitude of the supporting force to the urethra or bladder neck or other tissues is adequate to control leakage of urine during the stress event. In accordance with an example, the second signal may activate the actuation mechanism 108 so that the actuation mechanism 108 may allow controlled circulation of fluid through the elastomeric tubes 202 for adjustment of the supporting force. In accordance with various embodiments, the actuation mechanism 108 may be different. A few other actuation mechanisms and stimuli to stimulate the actuation mechanisms in accordance with embodiments are discussed elsewhere in the document without limitations.

In accordance with the embodiments discussed in conjunction with FIGS. 7-9, the implantable system 700 may be configured as a patient-controlled or subject-controlled adjustable urinary implantable system 700 that may be actuated manually by the subject when the subject senses increased intra-abdominal pressure or when the stress events occurs that may cause leakage of urine.

Figure 10:
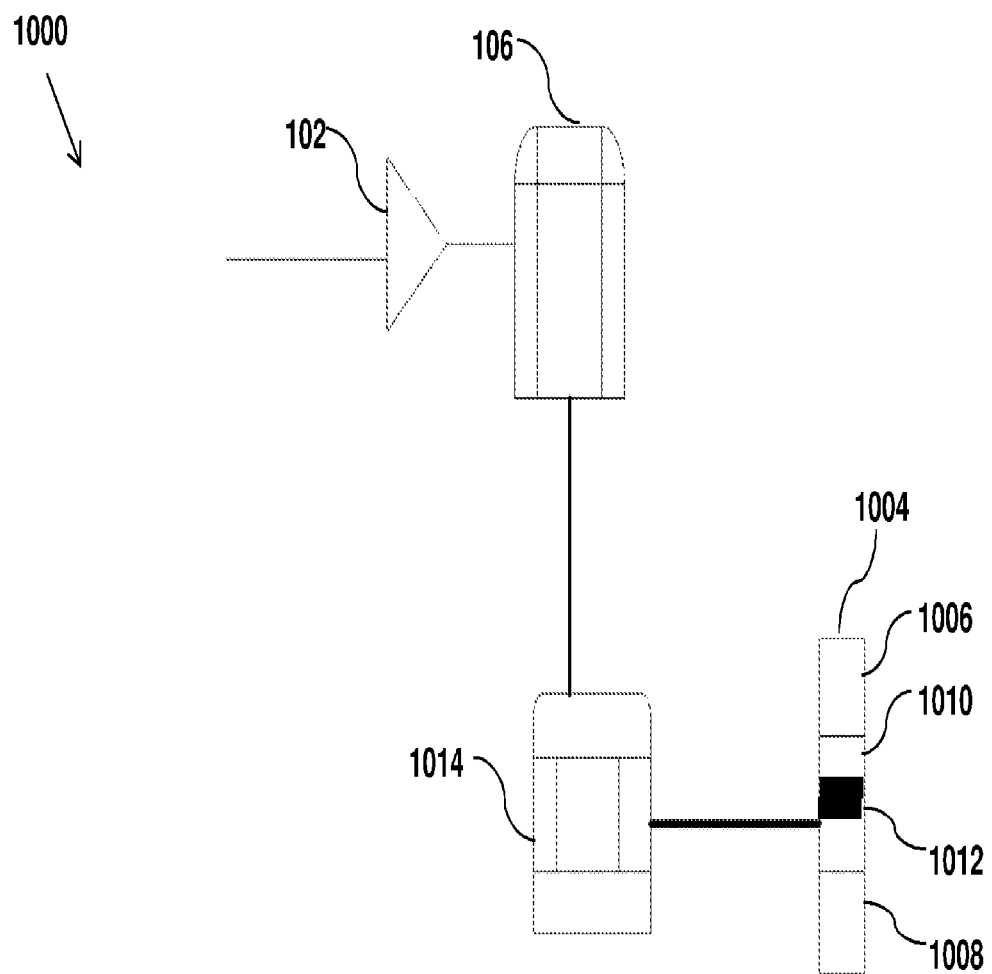
FIG. 10 illustrates a schematic diagram of an implantable system in accordance with an embodiment of the present invention.

FIG. 10 illustrates an implantable system 1000, in accordance with an embodiment of the present invention. The implantable system 1000 includes an implant 1002, the pressure sensor 102, and the processing circuit 106. The pressure sensor 102 and the processing circuit 106 may be similar to the pressure sensor 102 and the processing circuit 106 discussed in conjunctions with FIGS. 1 and 2A-2B.

Figure 11:
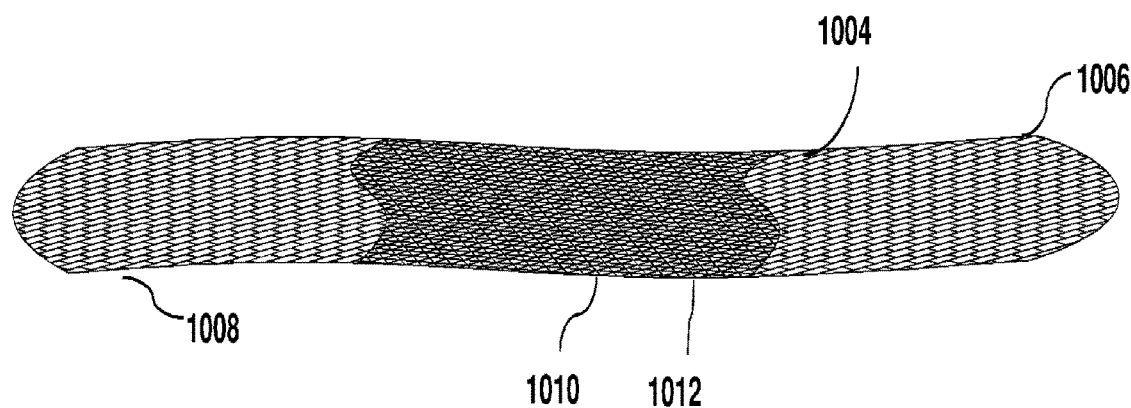
FIG. 11 illustrates a schematic diagram of an implant in accordance with an embodiment of the present invention.

FIG. 11 illustrates the implant 1002 in an embodiment of the present invention. The implant 1002 may be placed under a bladder neck or a mid-urethra or any other location to provide a support platform for controlling leakage of urine due to incontinence. The implant 1002 may include an elongate member 1004 with a first portion 1006, a second portion 1008, and a mid portion 1010 between the first portion 1006 and the second portion 1008 with a length of the implant 1002, extending between the first portion 1006 and the second portion 1008 longitudinally. The mid portion 1010 may be configured to support the urethra or bladder neck or other tissues at a target site. The implant 1002 may be similar to the implant 104 discussed in conjunctions with FIGS. 2A-2B except that the implant 1002 may include a shape memory element 1012 positioned at the mid portion 1010 of the implant 1002 that is configured to support the urethra or bladder neck or other tissues/locations. The shape memory element 1012 may serve as an actuating mechanism 1014 as an alternative to the actuating mechanisms of FIGS. 1 and 2A-2B to cause an adjustment of the tensioning force in the implant 1002 thereby changing magnitude of the supporting force to the urethra or bladder neck or other target site or tissues.

Referring to FIGS. 10 and 11, the implantable system 1000 is discussed herein. In an example, the shape memory element 1012 may be coupled to the mid portion 1010 separately. In an example, the mid portion 1010 may be fabricated with a shape memory material so that the mid portion 1010 itself may behave similar to the shape memory element 1012. In an example, the shape memory element 1012 may be fabricated from a shape memory polymer. In an example, the shape memory element may be fabricated from a shape memory alloy.

Examples of suitable shape memory materials that may be used for the shape memory element 1012 may include nickel-titanium alloy, copper-aluminum-nickel alloy, copper-zinc-aluminium-nickel alloy. In an example, the shape memory element 1012 may be made of Nitinol. In an example, the shape-memory polymer may in principle be a natural polymer, such as a "biopolymer." For example, the shape-memory polymer may be a protein or polysaccharide. Examples of proteins may include zein, casein, gelatin, glutin, serum albumin and/or collagen. Suitable polysaccharides may be selected, for example, from the group including alginate, celluloses, dextrans, pullulan, hyaluronic acid, chitosan and chitin. In an example, the shape-memory polymer may be a modified biopolymer. Examples of these may include cellulose derivatives, in particular, alkyl celluloses, hydroxyalkyl celluloses, cellulose ethers, cellulose esters, nitrocelluloses and chitosan. The alkyl celluloses may be, for example, methyl cellulose and/or ethyl cellulose.

Examples of suitable hydroxyalkyl celluloses may include hydroxyl-propyl cellulose, hydroxypropyl methyl cellulose and/or hydroxybutyl methyl cellulose. Other examples of cellulose derivatives that may be used are cellulose acetate, cellulose propionate, cellulose acetate butyrate, cellulose acetate terephthalate, carboxymethyl cellulose, cellulose triacetate and/or cellulose sulfate salts.

In an example, the shape-memory polymer may be a synthetic polymer. The possible synthetic polymers may be resorbable or non-resorbable polymers. Examples of possible synthetic non-resorbable polymers may be, for example, polyphosphazenes, polyamides, polyester amides, polyanhydrides, polycarbonates, polyacrylates, polyalkylenes, polyacrylamides, polyalkylene glycols, polyalkylene oxides, polyalkylene terephthalates, polyorthoesters, polyvinyl ethers, polyvinyl esters, polyvinyl halides, polyvinyl pyrrolidones, polyesters, polysiloxanes, polyurethanes, mixtures thereof and/or copolymers thereof. Suitable examples of non-resorbable polymers may include ethylene vinyl acetate, polyethylene, polypropylene, polystyrene, polyvinyl chloride, polyvinyl phenol, polymethyl methacrylate, polybutyl methacrylate, polyisobutyl methacrylate, polyhexyl methacrylate, polyisodecyl methacrylate, polylauryl methacrylate, polyphenyl methacrylate, polyhydroxypropyl methacrylate, polyethyleneglycol methacrylate, polymethyl acrylate, polyisopropyl acrylate, polyisobutyl acrylate, polyoctadecyl acrylate, polyhydroxyethyl acrylate, polyhydroxypropyl acrylate, polybutyl acrylate, mixtures thereof and/or copolymers thereof. Suitable resorbable polymers may further include polyhydroxy acids, preferably polylactides, polyglycolides, polyhydroxybutyric acid, polyhydroxyvaleric acid, polylactide-co-glycolides, polylactide-co-ε-caprolactone, polyglycolide-co-ε-caprolactone, polyamino acids, poly-pseudoamino acids, polyhydroxylalkanoates, polyvinyl alcohols, mixtures thereof and/or copolymers thereof. In an example, the shape memory element may be fabricated from a shape memory alloy. Other examples of suitable materials that may be used for the shape memory element 1012 may include nickel-titanium alloy, copper-aluminum-nickel alloy, copper-zinc-aluminum-nickel alloy, stainless steel, and the like.

The shape memory element 1012 may be capable of assuming an expanded configuration and an unexpanded configuration based on the second signal received from the processing circuit 106 that initiates a stimulus for changing configuration of the shape memory element 1012. In the expanded configuration, the tensioning of the mid portion 1010 may be increased thereby causing an increase in the supporting force to the urethra, bladder neck or any other tissue. In the unexpanded configuration, the mid portion 1010 may be relaxed so as to decrease tensioning in the mid portion 1010 or the elongate body member 1004 thereby decreasing the supporting force or entirely removing the supporting force as desired. In an example, the measure of expanding or unexpanding of the shape memory element 1012 may vary or may be controlled by the processing circuit 106 in view of a requirement as indicative from the intra-abdominal pressure variations identified through the first signal generated by the pressure sensor 102. The functioning of the pressure sensor 102 and the processing circuit 106 may be similar to as discussed in conjunction with FIGS. 1 and 2A-2B. For example, the shape memory element 1012 may expand more when the pressure sensor 102 senses a higher pressure than when a relatively lower pressure is sensed by the pressure sensor 102 during the stress event. The shape memory element 1012 may be configured to resume its shape during the unexpanded configuration. For example, the shape memory element 1012 may behave like a resilient membrane.

The pressure sensor 102 may be communicatively coupled with the processing circuit 106 and adapted to sense the intra-abdominal pressure or pressure variations transferred from the abdominal cavity. The pressure sensor 102 generates the first signal that is indicative of the intra-abdominal pressure or a change in the intra-abdominal pressure or pressure variations upon occurrence of the pressure event. The processing circuit 106 may be configured to process the first signal and generate the second signal that triggers the stimulus to cause a change in the configuration of the shape memory element 1012 embedded in the support mid portion 1010 of the elongate body member 1004 of the implant 1002. The stimulus resulting in the change in the configuration of the shape memory element 1012 causes an adjustment of the tensioning force in the elongate body member 1004 thereby changing magnitude of the supporting force to the urethra or bladder neck or other tissues at the target site. The shape memory element 1012 is configured to change its configuration between the unexpanded configuration and the expanded configuration in response to the second signal or the stimulus generated based on the second signal. In accordance with the illustrated embodiment, therefore, the present invention allows to automatically adjust the supporting force to the target site such as the urethra or bladder neck upon occurrence of the stress event based on automated sensing of the intra-abdominal pressure variations thereby preventing leakage of urine due to incontinence. The mid portion 1010 (referred to as support portion or support mid portion interchangeably) may remain relaxed or may provide only limited support most of the time when the intra-abdominal pressure is not large enough to cause leakage thus avoiding unnecessary application of the force to delicate tissues at urethra, bladder neck and the like. This may save the tissues from damage such as erosion, extrusion, infection, or from various other side effects.

Figure 12:
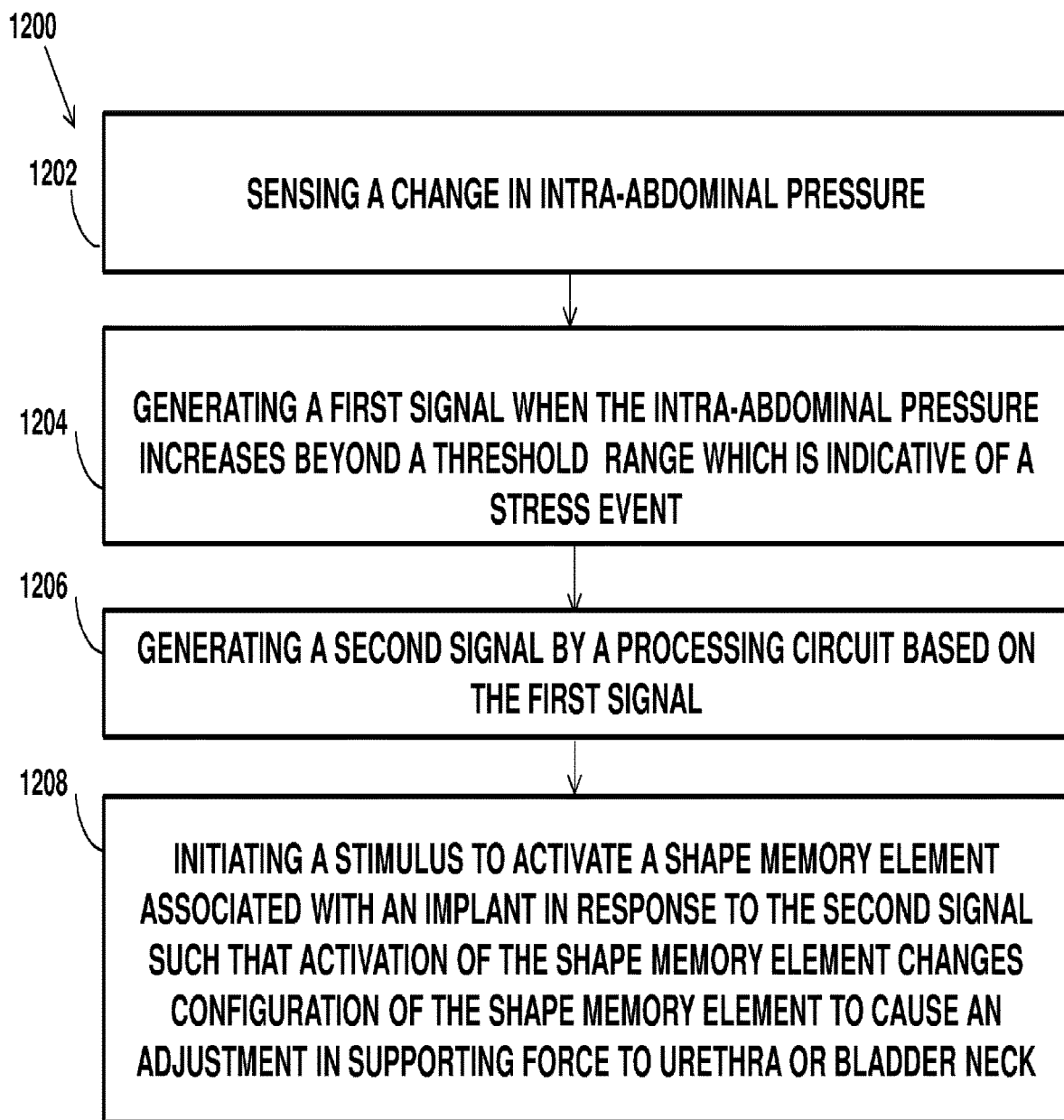
FIG. 12 illustrates a method diagram for operation of an implantable system in accordance with an embodiment of the present invention.

FIG. 12 illustrates a method diagram for operation of the implantable system 1000 of FIG. 10 in accordance with an embodiment of the present invention. The method 1200 of operation of the implantable system 1000 is now described hereafter referring to FIGS. 10-12. At step 1202, the method 1200 includes sensing a change in the intra-abdominal pressure. In an embodiment, the change in the intra-abdominal pressure may be sensed by the pressure sensor 102 located in or around or proximate to the abdominal cavity. In some embodiments, the pressure sensor 102 may be placed in or around or proximate to any other body cavity or to any other location if that gives a better reading of the intra-abdominal pressure or variations in the intra-abdominal pressure. The intra-abdominal pressure may rise due to events or activities, referred to as the pressure events or the stress events as discussed above. The sensing of the pressure by the pressure sensor 102 may be performed in a manner similar to as discussed in conjunction with FIGS. 1, 2A-2B, and 6.

At step 1204, the method 1200 includes generating the first signal when the intra-abdominal pressure increases beyond a threshold range which is indicative of the pressure or stress event. The first signal generated by the pressure sensor 102 may be indicative of the change in the intra-abdominal pressure upon occurrence of the pressure event or the stress event. The pressure sensor 102 may send the first sensed signal to the processing circuit 106 for further processing.

At step 1206, the method 1200 further includes generating the second signal by the processing circuit 106 based on the first signal. The steps of 1204 and 1206 may be similar to steps 604 and 606. The method 1200 may further include, at step 1208, initiating the stimulus to activate the shape memory element 1012 associated with the implant 1002 in response to the second signal such that activation of the shape memory element 1012 may change configuration of the shape memory element 1012 between the unexpanded configuration and the expanded configuration. The change in the configuration of the shape memory element 1012 may cause an adjustment in the supporting force to the urethra or bladder neck as per requirements. The supporting force may be adjusted such that the magnitude of the supporting force to the urethra or bladder neck or other tissues is adequate to control leakage of urine during the stress event. In an embodiment, the second signal may be sent by the processing circuit 106 to a stimulating source for changing the configuration of the shape memory element 1012 from the unexpanded configuration to the expanded configuration when the stress event occurs. Once the stress event is over and there is no more increased intra-abdominal pressure as sensed by the pressure sensor 102, the processing circuit 106 may generate a signal again to cause the shape memory element 1012 to regain its unexpanded configuration. For example, the method 1200 may also include generating a signal by the processing circuit 106 again to change the expanded configuration to the unexpanded configuration that allows the shape memory element 1012 to regain its shape when the intra-abdominal pressure reaches within the threshold range after the stress event is over.

In accordance with alternative or various embodiments, the present invention may include different ways to stimulate the shape memory element 1012 by employing different mechanisms to generate the stimulus such as different types of stimulation sources.

Figure 13:
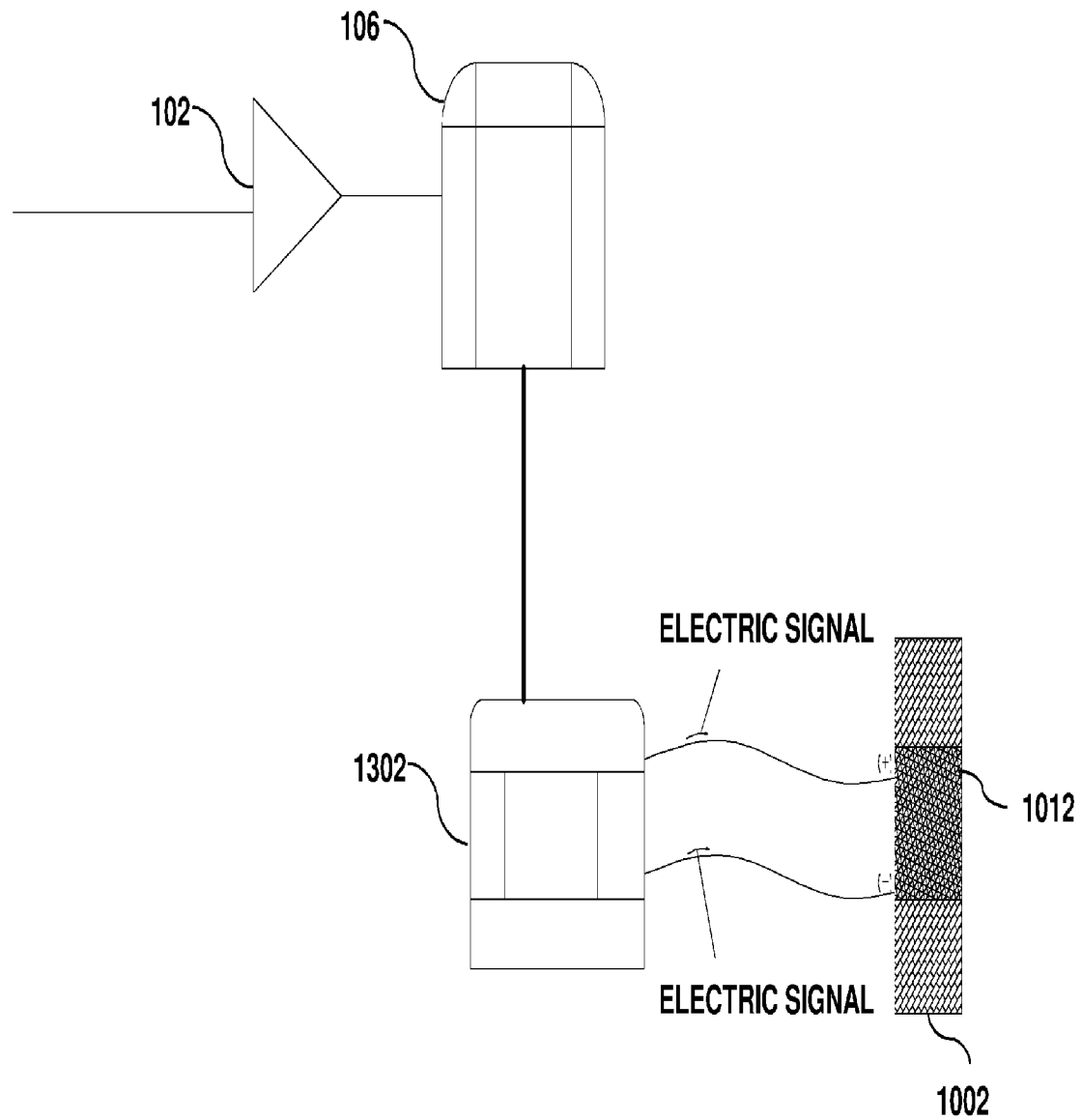
FIG. 13 illustrates a schematic diagram of an implantable system in accordance with an embodiment of the present invention.

In an example, as illustrated in FIG. 13, the shape memory element 1012 may include conducting shape memory polymer composites with carbon nanotubes that may be configured to be electro-active. FIG. 13 illustrates a schematic view of among other things the implant 1002 with such a shape memory element 1012 that communicates with the processing circuit 106 for managing support to the urethra or bladder neck or other tissues by application of an external electric field or electric energy from an electric source 1302. The implant 1002 may include a set of electrodes communicatively and operatively coupled with the electric energy source 1302. The electric energy source 1302 may generate an electric current that may serve as a stimulus to activate the electro-active shape memory element 1012. The processing circuit 106 may generate the second signal that initiates the stimulus and causes the electro-active polymer composites with carbon nanotubes to respond in accordance with the second signal. The processing circuit 106 may be programmed so as to generate the second signal to request a change in the configuration of the shape memory element 1012 from the unexpanded configuration to the expanded configuration when the stress event occurs and the pressure sensor 102 senses the increased intra-abdominal pressure. The processing circuit 106 may further be programmed to generate a signal again so as to request a change in the configuration of the shape memory element 1012 from the expanded configuration to the unexpanded configuration after the stress event is over and the urethra or bladder neck may not need any support or may require reduced support. In alternative embodiments, the shape memory element 1012 or shape memory polymer may include dielectric susceptible components other than the carbon nanotubes.

The shape memory element 1012 may comprise biodegradable shape memory polymers or alloys or non-biodegradable polymers or alloys.

In examples, the conducting shape memory polymer composites with short carbon fibers (SCFs), carbon black and metallic Ni powder, apart from the carbon nanotubes as discussed above, may be used. These conducting shape memory polymer composites may be developed by chemically surface-modifying multi-walled carbon nanotubes (MWNTs) in a mixed solvent of nitric acid and sulphuric acid, with the purpose of improving interfacial bonding between the polymers and conductive fillers in an embodiment. The shape-memory effect in these types of shape memory polymers may have been shown to be dependent on filler content and the degree of surface modification of the MWNTs, with the surface modified versions exhibiting good energy conversion efficiency and improved mechanical properties. The electro-active polymers may be characterized by their ability to expand and contract, such as a volumetric change, in response to electrical stimulation as generated by the electric source. Electro-active polymers may be divided into two categories such as electronic electro-active polymers (driven by an electric field) and ionic electro-active polymers (involving mobility or driven by diffusion of ions). Electronic electro-active polymers (electrorestrictive, electrostatic, piezoelectric, ferroelectric polymers) may be induced to change their dimensions by applied electric fields. Examples of materials in this class may include ferroelectric polymers, (commonly known polyvinylidene fluoride and nylon), dielectric electro-active polymers, electrorestrictive polymers such as the electrorestrictive graft elastomers and electro-viscoelastic elastomers, and liquid crystal elastomer composite materials wherein conductive polymers may be distributed within their network structure. The ionic electro-active polymers may include ionic polymer gels, ionomeric polymer-metal composites, conductive polymers and carbon nanotube composites. The induced displacement of both electronic electro-active polymers and ionic electro-active polymers may be geometrically designed to bend, stretch, contract or rotate. The ionic electro-active polymers may bend significantly upon application of a small voltage, such as 1 or 2 volts, and thereby facilitate proper design of a substrate.

The ionic electro-active polymers may possess a number of additional properties that may make them ideal, for use in the implantable devices of the present invention. In an example, the ionic electro-active polymers may be lightweight, flexible, small and easy to manufacture. Further the energy sources may be available, which may be easy to control, and thereby the energy may be easily delivered to the electro-active polymers. In other example, the ionic electro-active polymers may show small changes in potential (e.g., potential changes on the order of 1 volt). Furthermore the ionic electro-active polymers may be used to effect volume change in the electro-active polymers. In an example, the ionic electro-active polymers may be relatively fast in actuation (e.g., full expansion/contraction in a few seconds).

In accordance with the embodiments discussed above in conjunction with FIGS. 10-13, the implantable system 1000 may be activated automatically based on automatically sensing of the intra-abdominal pressure or pressure variations by the pressure sensor 102. In other embodiments, however, the implantable system 1000 may be controlled by the subject when there is a possibility of leakage of urine such as due to increased abdominal pressure and/or due to occurrence of the stress event. In such embodiments, the implantable system 1000 may include a trigger unit similar to the trigger unit 702 discussed in conjunctions with various figures that may be activated manually by the subject. The trigger unit when activated may generate the first signal which may cause the processing circuit 106 to generate the second signal and initiate the stimulus to activate the shape memory element 1012 for changing its configuration. In accordance with an embodiment of the trigger unit discussed in conjunction with various figures, the trigger unit may be subcutaneously placed or may be provided externally such as in the form of a programmer or a controller.

Figure 14:
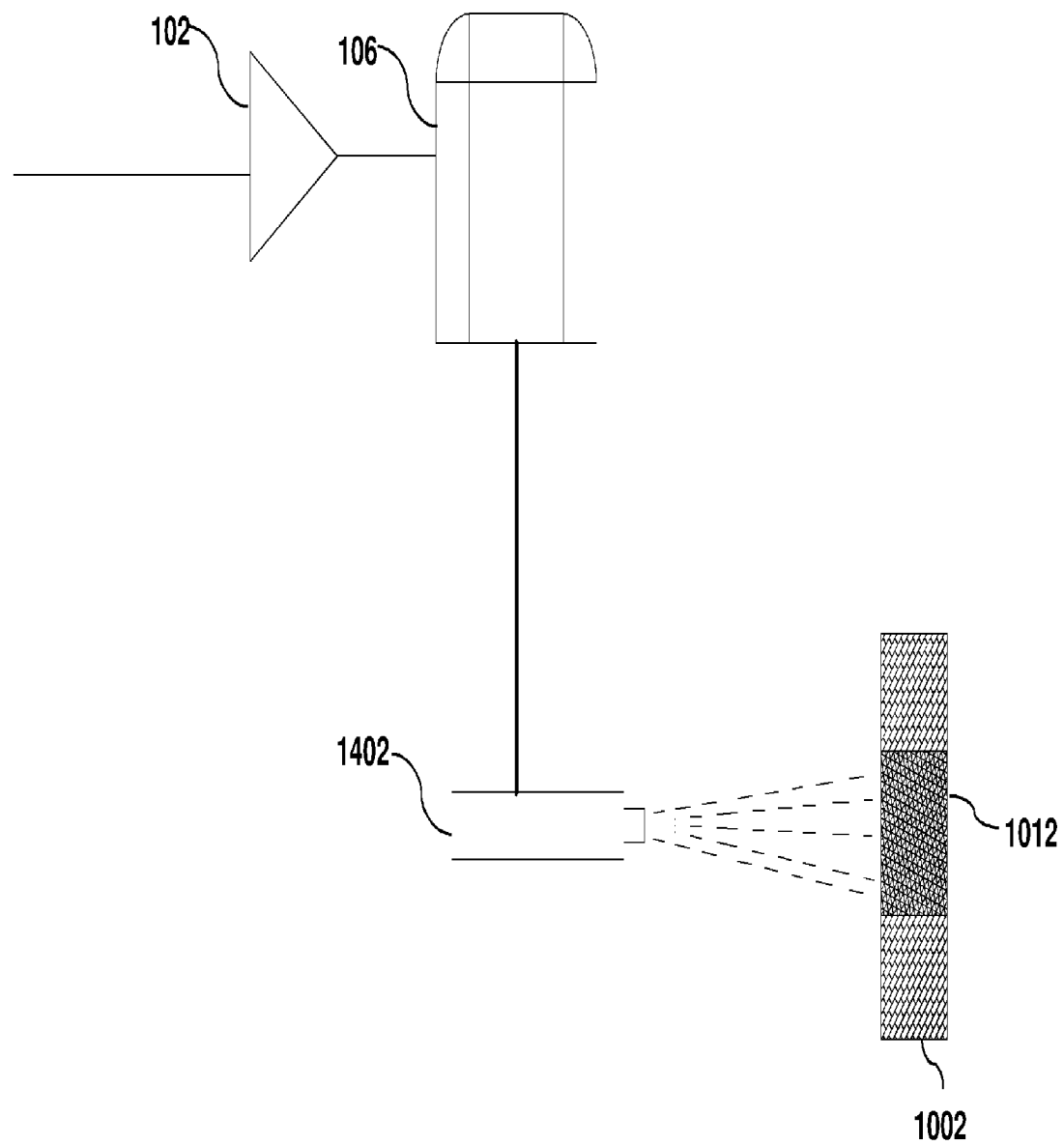
FIG. 14 illustrates a schematic diagram of an implantable system in accordance with an embodiment of the present invention.

In an example, as illustrated in FIG. 14, the shape memory element 1012 may include light induced or photoresponsive shape memory polymers configured to be activated by a light beam or photon ejected from a light energy source 1402. FIG. 14 illustrates a schematic view of among other things the implant 1002 with such a shape memory element 1012 that communicates with the processing circuit 106 for managing support to the urethra or bladder neck or other tissues by application of light energy or photon from the light energy source 1402. The light-induced or photoresponsive shape memory element 1012 is coupled with or integrated with the elongate body member 1004 of the implant 1002 such that the shape memory element 1012 is configured to deform from an initial state to a deformed state (the unexpanded state to the expanded state) in response to the light beam or photon. The deformation in the shape memory element 1012 allows for adjustments in tensioning force provided to the elongate body member 1004 upon occurrence of the pressure event. The light energy source 1402 may generate the light beam or photon that may serve as the stimulus to activate the photoresponsive shape memory element 1012. The processing circuit 106 may generate the second signal that causes to initiate the stimulus or eject a photon or light beam which eventually causes the photoresponsive shape memory element 1012 to respond in accordance with the second signal. The processing circuit 106 may be programmed so as to generate the second signal to request a change in the configuration of the shape memory element 1012 from the unexpanded configuration to the expanded configuration when the stress event occurs and the pressure sensor 102 senses the increased intra-abdominal pressure. The processing circuit 106 may further be programmed to generate a signal so as to request a change in the configuration of the shape memory element 1012 from the expanded configuration to the unexpanded configuration after the stress event is over. The shape memory element 1012 may comprise biodegradable shape memory polymers or alloys or non-biodegradable polymers or alloys. In a manner similar to as discussed above, in some embodiments, the photoresponsive shape memory element 1012 may be activated by the processing circuit 106 based on the first signal generated by the trigger unit manually instead of automated detection of pressure variations and automated adjustment of the supporting force.

The photoresponsive shape memory element 1012 implanted in a patient's body may be heated non-invasively using, for example, light energy sources such as infrared, near-infrared, ultraviolet, microwave and/or visible light sources. The light energy may be selected to increase absorption by the shape memory element and reduce absorption by the surrounding tissue. Thus, damage to the tissue surrounding the shape memory element 1012 may be reduced when the shape memory element 1012 is heated to change its shape. Energy absorbing materials for light or laser activation energy may include nanoshells, nanospheres and the like, particularly where infrared laser energy is used to energize the material. Such nanoparticles may be made from a dielectric, such as silica, coated with an ultra thin layer of a conductor, such as gold, and be selectively tuned to absorb a particular frequency of electromagnetic radiation. Coatings comprising nanotubes or nanoparticles can also be used to absorb energy from the light energy source or inductive heating, or the like.

Suitable photosensitive networks or materials or polymers to be used in the shape memory element 1012 may be amorphous and may be characterized by covalent network points, which may determine the configurations of the shape memory element 1012. The shape memory polymers with a photosensitive induced shape memory effect, which may respond to a particular wavelength of light as the transition stimulus, may have photo-reactive groups, which may reversibly be linked with one another by irradiation with light. These photo-reactive groups may take over the function of the switching segment in the shape memory polymers with thermal transitions. The programming of a temporary shape and re-generation of the permanent shape may take place by irradiation without a change in temperature. Non-limiting examples of photoresponsive switches may include cinnamic acid and cinnamylidene acetic acid.

In accordance with various embodiments, the implants discussed in conjunction with various figures above may be implanted through a transvaginal or an abdominal approach or any other approach. In some embodiments, the implants can be used to suspend various bodily locations in a body of a patient such as pelvic organ of a patient's body. In some embodiments, the implants can be used in a urinary sling. In some embodiments, the implants can be used in a retropubic incontinence sling. In some embodiments, the implants can be configured to be delivered by way of a transvaginal approach or a transobturator approach or vaginal pre-pubic approach or a laparoscopic approach or can be delivered through other methods and may be positioned at various locations within a patient's body without limitations.

The implant as discussed in various embodiments herein such as 104 may be delivered inside a patient's body through a surgical procedure. In some embodiments, the implant 104 is inserted inside the body through a laparoscopic approach. For example, the method may include creating an abdominal incision for delivering the implant 104 inside the body laparoscopically. In some embodiments, the implant 104 is delivered through a transvaginal approach. The procedure may include placing the implant 104 at a target site underneath the urethra or bladder neck so that the intermediate portion such as 306 supports the urethra. Subsequently, after the procedure is complete, bodily incisions may be closed after appropriate tensioning and fixation of the implant 104. The method may include making two contra lateral abdominal incisions. The method may further include making a vaginal incision. Other components of the implantable system such as 100 may be deployed inside the body through various incisions at various locations. For example, the pressure sensor 102 may be placed in the abdominal cavity in an embodiment. The processing circuit 106 and the actuating mechanism 108 may be placed subcutaneously in an embodiment. The implants and implantable systems as discussed in conjunction with various other figures throughout the document may be deployed in a similar manner or in any other manner without limitations.

In accordance with some embodiments, the shape memory element 1012 may be activated to change its configuration between the expanded configuration and the unexpanded configuration through various other stimuli. For example, in an embodiment, the shape memory element 1012 may be activated by a magnetic field or electromagnetic field. In example, the shape memory element 1012 may be triggered upon application of an external stimulus including one or more of a temperature change, electric or magnetic field, light, pH and solution such as water-driven actuation of shape memory polymers. In other examples, various transition stimuli such as IR radiation, NIR radiation, UV radiation and the like, may be radiated to the shape memory polymer. The shape memory elements with polymers with a thermally induced shape memory effect may respond to a thermal transition stimulus which may have at least one switching segment with a transitional temperature. The switching segments may form temporary cross linking portions, which may resolve when heated above the transitional temperature and which form again when being cooled. At this temperature, the shape memory polymer may show a change in shape. In addition, other external stimuli may trigger the transition between shapes, such as moisture.

In accordance with some embodiments as discussed above in conjunction with various figures, the implantable system such as 100 or 1000 may include various other types of implants. The implant may be for example an artificial urinary sphincter (also referred to as sphincter for the purpose of simplicity of description without limitations). The artificial urinary sphincter may be a cylindrical shape structure configured to be positioned to a target site for preventing leakage of urine. The sphincter may include an outer cuff having inner and outer portions for positioning proximate urethra. The sphincter may include an inner shape memory element cuff fabricated from a shape memory polymer or shape memory alloy encircling the inner portion of the outer cuff and configured to be directly in contact with the urethra. The shape memory element cuff may be electro-conductive in an example. The pressure sensor 102 as discussed above may be communicatively coupled with the inner shape memory element cuff and the outer cuff and adapted to sense the intra-abdominal pressure transferred from an abdominal cavity or intra-abdominal variations. The pressure sensor 102 may generate the first signal that is indicative of a change in the intra-abdominal pressure upon occurrence of a pressure event. The processing circuit 106 processes the first signal sensed by the pressure sensor 102 and generates the second signal causing to contract the inner cuff to cause compression in the urethra. The inner shape memory element cuff is configured to deform from an initial state to a deformed state in response to the second signal received from the processing circuit. A deformation in the inner shape memory element cuff may allow for adjustments in tensioning force or may contract urinary passage upon occurrence of the pressure event. In an example, the inner shape memory element cuff may include conducting shape memory polymer composites with carbon nano-tubes that may be configured to be electro-active. The compression or deformation in the sphincter may be automatically controlled through the sensed intra-abdominal variations in an example. In an example, activation of the sphincter may be controlled manually by a user based on requirements such as with the use of a trigger unit similar to the trigger unit 702 discussed earlier. The trigger unit 702 may be subcutaneously placed and configured to be activated manually by a subject upon his desire arising out of changing abdominal pressures transferring from an abdominal cavity or out of other physiological conditions. The trigger unit 702 may be configured to generate the first signal upon activation by the subject. The processing circuit 106 may generate the second signal based on the first signal. The inner shape memory element cuff may be configured to deform from the initial state to the deformed state in response to the second signal received from the processing circuit 106 such that the deformation in the cuff allows for adjustments in the tensioning force provided to the urethra or may allow contracting of urinary passage upon occurrence of the pressure event.

In accordance with an embodiment, the sphincter may be communicatively coupled to a light source that may emit a light beam or photon upon receipt of the second signal from the processing circuit 106. The inner shape memory element cuff may be fabricated from a light-induced shape memory polymer or alloy and coupled with the outer cuff or formed monolithically along with the outer cuff. The inner shape memory element cuff is configured to deform between the initial state and the deformed state in response to the light beam or photon originated from the light source. The light source may be similar to as discussed earlier in conjunction with various figures.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

The invention claimed is:

1. An automatically adjustable implantable system for managing urinary incontinence, the implantable system comprising:
   a sling having an elongate body member with a proximal portion, a distal portion and an intermediate portion, wherein the intermediate portion is configured to be positioned underneath a urethra of a patient;
   a pressure sensor communicatively coupled with the elongate body member and adapted to sense intra-abdominal pressure transferred from an abdominal cavity, the pressure sensor generating a first signal that is indicative of a change in the intra-abdominal pressure upon occurrence of a stress event;
   a processing circuit to process the first signal sensed by the pressure sensor, wherein the processing circuit is configured to generate a second signal causing adjustment of a tensioning force in the elongate body member thereby changing a magnitude of a supporting force to the urethra; and
   a shape memory polymer member comprising ionic electro-active polymers at least one of coupled with or integrated with the elongate body member, wherein the shape memory polymer member is configured to deform from an initial state to a second state via the ionic electro-active polymers in response to the second signal received from the processing circuit, wherein the deformation in the shape memory polymer member allows for adjustments in the tensioning force provided to the elongate body member responsive to the occurrence of the stress event.

2. The automatically adjustable implantable system of claim 1, wherein the shape memory polymer member includes conducting shape memory polymer composites with carbon nanotubes that are configured to be electro-active, wherein a transition between the initial state and the second state is triggered by an electric stimulus that activates the shape memory polymer composites.

3. The system of claim 1, wherein the deformation in the shape memory polymer member allows for adjustments in tensioning force provided to the elongate body member.

4. The system of claim 1, wherein the processing circuit is configured to generate the second signal based on one or more indications of bladder fullness or bladder emptiness.

5. The system of claim 1, wherein the intermediate portion is fabricated as the shape memory polymer member comprising ionic electro-active polymers.

6. A subject-controlled implantable system for managing urinary incontinence, the system comprising:

an elongate body member with a proximal portion, a distal portion and an intermediate portion, wherein the intermediate portion is configured to be positioned underneath a urethra of a subject;

a trigger unit configured to be subcutaneously placed and configured to be activated manually by the subject responsive to changing abdominal pressures transferring from an abdominal cavity, the trigger unit configured to generate a first signal upon activation by the subject, wherein the first signal includes a request for causing an adjustment of tensioning force in the elongate body member;

a processing circuit to process the first signal, wherein the processing circuit is configured to generate a second signal responsive to the request causing an adjustment of tensioning force in the elongate body member thereby changing a magnitude of a supporting force to the urethra; and a shape memory polymer member comprising ionic electro-active polymers at least one of coupled with or integrated with the elongate body member, wherein the shape memory polymer member is configured to deform from an initial state to a second state via the ionic electro-active polymers in response to the second signal received from the processing circuit, wherein the deformation in the shape memory polymer member allows for adjustments in tensioning force provided to the elongate body member.

7. The system of claim 6, wherein the deformation in the shape memory polymer member allows for adjustments in tensioning force provided to the elongate body member responsive to activation of the trigger unit.

8. The system of claim 6, wherein the processing circuit is configured to generate the second signal based on one or more indications of bladder fullness or bladder emptiness.

9. The system of claim 6, wherein the intermediate portion is fabricated as the shape memory polymer member comprising ionic electro-active polymers.

* * * * *